United States Patent [19]
Koths et al.

[11] Patent Number: 5,965,382
[45] Date of Patent: Oct. 12, 1999

[54] NUCLEIC ACID ENCODING SECRETED MAC-2 BINDING GLYCOPROTEIN

[75] Inventors: Kirston E. Koths, El Cerrito; Robert F. Halenbeck, San Rafael; Eric W. Taylor, Berkeley; Alice M. Wang, Lafayette; Clayton L. Casipit, Hayward, all of Calif.

[73] Assignee: Chiron Corporation, Emeryville, Calif.

[21] Appl. No.: 08/316,714

[22] Filed: Sep. 29, 1994

Related U.S. Application Data

[63] Continuation of application No. 07/961,404, Oct. 15, 1992, abandoned, which is a continuation-in-part of application No. 07/777,121, Oct. 16, 1991, abandoned.

[51] Int. Cl.⁶ .................................................. C12N 15/12
[52] U.S. Cl. ................ 435/69.1; 435/252.3; 435/254.11; 435/320.1; 435/325; 536/23.5; 536/24.31
[58] Field of Search ............................... 435/69.1, 240.1, 435/320.1, 252.3, 254.11, 325; 536/23.1, 23.5, 24.31; 530/350, 395

[56] References Cited

U.S. PATENT DOCUMENTS 5,298,391  3/1994  Iacobelli ........................................ 435/2
5,422,265  6/1995  Civelli et al. .......................... 435/252.3

FOREIGN PATENT DOCUMENTS 0 453 419 B1  4/1996  European Pat. Off. .
WO93/16183  8/1993  WIPO .

OTHER PUBLICATIONS

Rosenberg et al., *J. Biol. Chem.*, 266, 18731–18736, Oct. 1991.
Pierce et al., *Eur. J. Biochem.*, 196, 177–184, 1991.
A. Aruffo, et al., *Journal of Experimental Medicine* (1991) 174:949–952.
T. Maniatis, et al., *Molecular Cloning* (1989) 2nd Edition 9.47–9.55.
Ulrich et al., *J. Biol. Chem.* (1994) 269(28):18401–18406.
Friedman et al., *Proc. Natl. Acad. Sci. USA* (1993) 90:6815–6819.
Natali et al., *Cancer Research* (1982) 42:583–589.
Iacobelli et al., *Fed. of European Biochem. Soc.* (1993) 319(1,2,):59–65.
Freeman et al., *Proc. Nat'l. Acad. Sci.*, (87):8810–8814 (1990).
Matsumoto et al., *Proc. Nat'l. Acad. Sci.*, (87):9133–9137 (1990).
Kodama et al., *Nature*, (343):531–535 (1990).
Woo et al., *Journal of Biological Chemistry*, (265):7097–7099 (1990).
Ho et al., *J. Immunology*, (128):1221–1228 (1982).
Cherayil et al., *Proc. Nat'l. Acad. Sci.*, (87):7324–7328 (1990).
Jia et al., *J. Biol. Chem.*, (263):6009–6011 (1988).
Oda et al., *Gene*, (99):279–283 (1991).
Newburg et al., *Pediatric Research*, (31):22–28 (1992).
Lonnerdal, *American Journal of Clinical Nutrition*, (42):1299–1317 (1985).
Sharon et al., *Science*, (246):227–246 (1989).
Dupuis et al., *Can. J. Biochem. Cell. Biol.*, (63):932–940 (1985).
Drickamer, *J. Biol. Chem.*, (263):9557–9560 (1988).
Holmgren et al., *Infection and Immunity*, (39):147–154 (1983).
Zajac et al., *Journal of General Virology*, (72):1667–1675 (1991).
Laegreid et al., *Acta. Paediatr. Scand.*, (75):696–701 (1986).
Leffler et al., *Journal of Biological Chemistry*, (261):10119–10126 (1986.
Raz et al., *Int. J. Cancer*, (46):871–877 (1990).
Allan et al., *Exptl. Cell. Res.*, (78): 271–278 (1973).
Alexander et al., *Biochimica et Biophysica Acta*, (512):350–364 (1978).
Frigeri et al., *J. Immunology*, (148):861–867 (1992).
Lasky et al., *Cell*, (69):927–938 (1992).
Koths, et al., *J. Biol. Chem.*, (268):14245–14249 (1993).
Mierendorf et al., Methods in Ienzymology, vol. 152, pp. 458–469, 1987, Academic Press.
Rosenberg et al., 1991, J. Biol. Chem., 266, 18731.
Linsley et al., 1986, Biochemistry, 25, 2978.
Jacobs et al., 1985, Nature, 313, 806.
Phillips, "The Involucrin Gene of the Galago", *J. Biol. Chem.*, (1990), 265(14):7804–7807.

*Primary Examiner*—Sally P. Teng
*Attorney, Agent, or Firm*—Fish & Richardson; Paul B. Savereide; Robert P. Blackburn

[57] ABSTRACT

A purified glycoprotein complex of over 1200 kD apparent native molecular weight having a sedimentation value of approximately 25S and having the ability to selectively bind human Mac-2 or interfere with PHA activation of lymphocytes, DNA sequences that encode the protein, and expression systems for expressing it, thus providing for medicaments that are useful for treating or diagnosing diseases, including cancer, infectious disease, and diseases of the immune system.

22 Claims, 7 Drawing Sheets

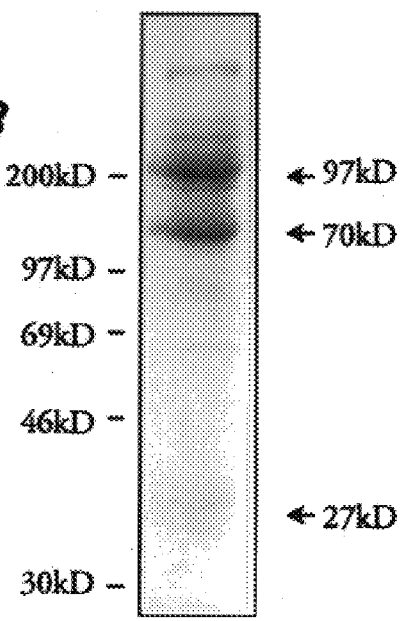
SDS-PAGE
(Coomassie stain)
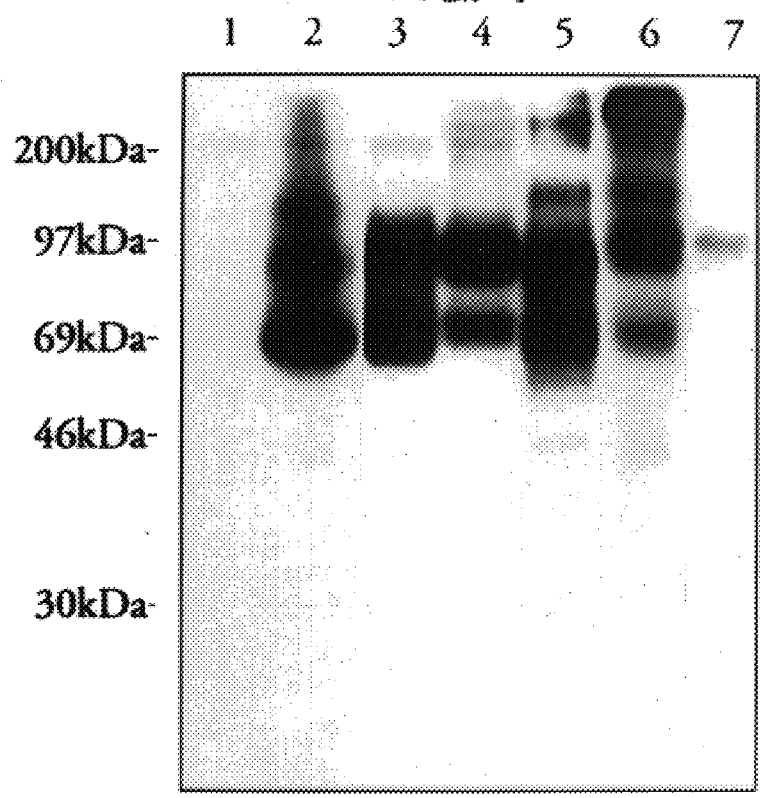

SDS-PAGE
(Coomassie stain)

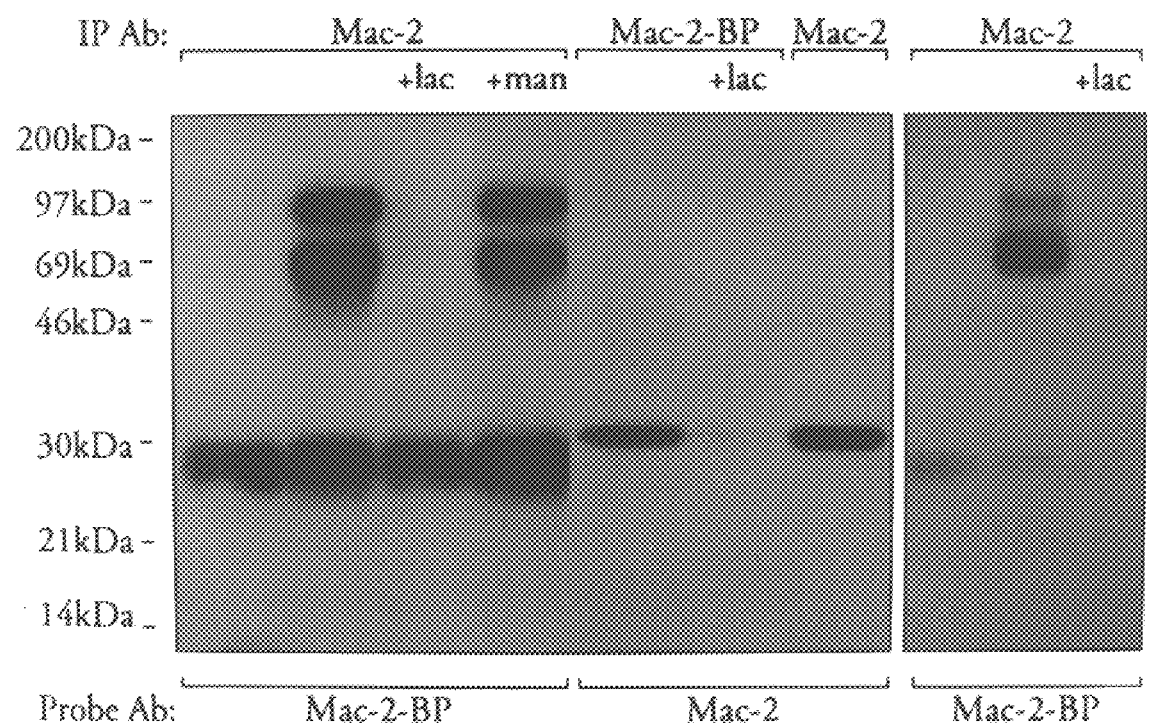

NUCLEIC ACID ENCODING SECRETED MAC-2 BINDING GLYCOPROTEIN

CROSS REFERENCE TO RELATED APPLICATION

This application is a continuation of application Ser. No. 07/961,404, filed Oct. 15 1992 now abandoned, which is a continuation-in-part of Ser. No. 07/777,121 filed on Oct. 16, 1991, now abandoned.

FIELD OF THE INVENTION

This invention is in the area of molecular biology/biochemistry and presents a purified glycoprotein that binds to the human lectin Mac-2, and would play an important role in interaction events at cell surfaces, DNA sequences that encode the protein, and expression systems for expressing it. The protein has a variety of medical applications involving the regulation of cell surface interactions relating to immune responses, pathogen/host cell interactions, metastasis, and cell adhesion and migration, and developmental functions such as pre-antibody immunity.

BACKGROUND OF THE INVENTION

Cell surface molecules play a key role in the infectivity of viruses and other pathogens with their target cells. For example, ICAM-1, the endothelial cell receptor for integrin binding, is also the receptor for rhinovirus binding. Rhinoviruses are members of the picornavirus family and are responsible for about 50% of common colds in humans. Another classic example of such interactions is influenza hemagglutinin, a lectin that binds to sialic acid on its host cell as the first step in infection. Thus, a prophylactic approach to preventing the common cold is to interfere with the binding of rhinovirus to cell-bound ICAM-1 by administration of soluble binding competitors to the host receptor.

Lectins are a class of proteins that bind carbohydrates specifically and noncovalently. Lis, H. and Sharon, N., 1986, Annual Review of Biochemistry, 55:35. Numerous lectins have been identified in higher animals, both membrane-bound and soluble, and have been implicated in a variety of cell-recognition phenomena, in addition to roles that they play in metastasis.

Lectins may generally be classified as either of the C-type, whose binding properties are calcium-dependent and which are structurally related to the asialoglycoprotein receptor, or the S-type, or thiol-dependent lectin. It should be noted, however, that there are other proteins with lectin properties that apparently do not fall into either of these classes, such as for example, fibronectin and laminin. Drickamar, K., 1988, J. Biol. Chem., 263:9557.

Lectins are thought to play a role in regulating cellular events that are initiated at the level of the plasma membrane. For instance, plasma membrane associated molecules are involved in the activation of various subsets of lymphoid cells, particularly T-lymphocytes, and it is known that cell-surface molecules are responsible for activation of these cells and consequently their response during an immune reaction. This phenomenon has been studied using various plant lectins, such as leucoagglutinating phytohaemagglutinin (PHA) and concanavalin A (con A). These molecules are thought to activate T-cells by binding to carbohydrate moieties associated with specific molecules on the T-lymphocyte cell surface.

One known human lectin, originally described as a cell-associated macrophage antigen, is called "Mac-2". Ho & Springer, J. Immunol., (1982) 128:1221–1228. The 32-kDa lectin Mac-2, is expressed at significant levels in thioglycolate-elicited mouse macrophages but not in resident macrophages and may be involved in cell adhesion or immune responses. The human homologue of Mac-2 has been cloned and shown to be a lactose/galactose-specific lectin that is externalized, despite lacking a leader sequence. Oda et al., Gene (1991) 99:279–283; Cherayil et al., PNAS (USA) (1990) 87:7324–7438. Mac-2 is identical or closely related to other previously described lectins: EBP, a protein believed to represent a new type of cell adhesin (Frigeri & Liu, J. Immunol. (1992) 148:861–867), CBP35, a galactose-binding lectin (Jai & Wang, J. Biol. Chem. (1988) 263:6009–6011), a non-integrin laminin-binding protein (Woo et al., J. Biol. Chem. (1990) 265:7097–7099), RL-29, a lactose-specific lung lectin (Leffler & Barondes, J. Biol. Chem. (1986) 261:10119–10126), and L-34, a galactose-binding lectin correlated with neoplastic transformation and metastasis (Raz et al., Int. J. Cancer (1990) 46:871–877). Mac-2 is present in significant concentrations in the tips of intestinal villi, where it may be a target for colonization by human pathogens.

Several researchers have isolated and purified glycoproteins that act as ligands for various lectins. For example, a protein termed the tamm-horsfall glycoprotein has been shown to inhibit lymphocyte activation induced by several lectins, including leucoagglutinin and hemagglutinin from Phaseolus vulgaris. Serafini-Cessi, F. et al., 1979, Biochemical Journal, 183:381–388. Additionally, glycoproteins that act as PHA-binding factors have been partially purified from porcine splenic lymphocytes. Further studies also show that PHA activation of porcine lymphocytes is inhibited by the partially purified glycoproteins. Dupuis, G. et al., 1985, Canadian Journal of Biochemistry & Cell Biology, 63:932–940. These researchers were unable to identify a precise molecular weight species that exhibited the inhibitory activity. Rather, they reported a range of molecular weight species in partially purified preparations, as revealed by Coomassie Blue staining of sodium dodecyl sulphate polyacrylamide gels. Major bands were observed having apparent molecular weights of about 50–55, 75, 95, 130, and 155 kD; additional minor species exhibited apparent molecular weights of about 42, 45, 60–65, 175, and 200–250 kD.

Similar studies by other investigators have shown the existence of other PHA-binding molecules. For instance, a PHA-binding factor from pig mesenteric lymph nodes has been isolated and shown to have a molecular mass of about 100 kD. Allan, D. and Crumpton, N. J., 1973, Exp. Cell Res., 7:271–278. A PHA-binding molecule present in plasma membranes from pig submaxillary lymph node lymphocytes was shown to exhibit an apparent molecular mass greater than 94 kD. Alexander, S. et al., 1978, Biochemical Biophys. Acta, 512:350–364. Other PHA-binding ligands have been isolated from human peripheral blood by affinity chromatography and have been found to have molecular masses in the range of 20–35, 43, 60, and 70 kD. Skoog, B. et al., 1980, Scand. Journal Immun., 11:369–376. Other researchers have reported the presence of leucoagglutinin-receptor glycoproteins with molecular weights ranging from 43 to 250 kD in neuraminidase-treated peripheral human T lymphocytes.

The health benefits of human breast milk have long been recognized. Recently, the prophylactic effects of milk in preventing gastrointestinal infections have been described. Gerrard, J., 1974, Pediatrics, 54:757–764. At least in part, this is due to non-immunoglobin glycoproteins present in milk that have binding properties that protect newborns from viral or bacterial infections. Lonnerdal, B., 1985, Am. J. Clin., 42:1299–1317 and Holmgren, J. et al., 1983, Infect. Immun., 33:459–463. These proteins are thought to exert their effects, at least in part, by preventing or disrupting the adherence of bacteria or viruses to intestinal epithelium by binding to bacterial adhesins or viral hemagglutinins. Bacterial adhesins and viral hemagglutinins are surface molecules that facilitate the adherence of these organisms to epithelial cell surfaces as an early step in infection. The milk proteins involved in this process have not been well characterized. Holmgren, J. et al., 1983, Infect. Immun., 33:459–463. However, a glycoprotein having a molecular weight above 400,000 has been described that is able to neutralize respiratory syncytial virus. Laegreid, A. et al., 1986, Acta Paediatric. Scand., 75:696–701. In addition to the immuno-protective and anti-infective functions provided by such proteins, other human milk proteins serve special roles as carriers of specific nutrients.

Similarly, a high molecular weight material has been identified in human serum that interferes with the attachment and infectivity of hepatitis A virus to various cell lines. Zajac, A. et al., 1991, J. of Gen. Virol, 72:1667–1675. This material has not been purified nor have its properties been further characterized.

Rosenberg et al., J. Biol. Chem. (1991) 266:18731–18736, describe a Mac-2 binding protein from colon carcinoma cells, and report a partial N-terminal protein sequence. Linsley et al., Biochem. (1986) 25:2978–2986 have characterized a lung carcinoma protein, L3, with a identical N-terminal protein sequence. No one has as yet identified the complete amino acid sequence for a novel glycoprotein specific for binding to the human Mac-2 lectin, nor has the cDNA encoding such a sequence been cloned.

SUMMARY OF THE INVENTION

An object of the invention is the description of a substantially purified protein that binds to the Mac-2 lectin. This "Mac-2 binding protein" has an apparent native molecular weight of over 1200 kD, a sedimentation value of approximately 25S, and is composed of glycosylated subunits having approximately 567 amino acids. Depending on the source and degree of glycosylation, the apparent molecular weight of the unproteolyzed subunits is about 85–97 kD as revealed by SDS gel electrophoresis.

A second object of the invention is the description of DNA sequences that encode the subunits, and vectors for expressing the protein encoded by the sequences.

A third object of the invention is the description of medicaments consisting of the lectin-binding protein that are useful in treating or preventing diseases that result from binding of a disease-causing agent to the cell surface of a target cell.

A fourth object of the invention is the description of medical diagnostics, preferably antibody in nature, for determining the concentration of gp85–97 protein in biological fluids, which information can be predictive of the health status of an individual including the susceptibility of the individual to disease. A preferred application is in monitoring the concentration of gp85–97 protein in human milk to determine if an infant is receiving the appropriate amount of this protein for maximum health benefit.

A fifth object of the invention is a composition consisting of infant formulas supplemented with gp85–97 protein, either recombinant or the purified native protein, that can be fed to an infant in need of the medical benefit afforded by the protein.

A sixth object of the invention is the presentation of methods of treating cancer, preferably breast cancer, consisting of administering the molecule in amounts effective to treat the cancer.

A seventh object of the invention is a method for treatment of infectious diseases in a patient, preferably those caused by pathogens that colonize nasal passages or intestinal epithelium, consisting of administering to a patient in need of such treatment a therapeutically effective amount of gp85–97 and a pharmaceutically acceptable carrier.

These and other objects of the invention will become apparent upon reading the following description of the invention.

BRIEF DESCRIPTION OF THE DRAWINGS

FIG. 2B shows a SDS-PAGE analysis of a representative preparation of purified gp97.

FIG. 7 shows a Western blot analysis of various human fluids with anti-gp85–97 antibody.

FIG. 8 shows a Western blot analysis of a co-precipitation of gp 85–97 from HT-29 (FIG. 8A) and HL-60 (FIG. 8B) cells.

Figure 1:
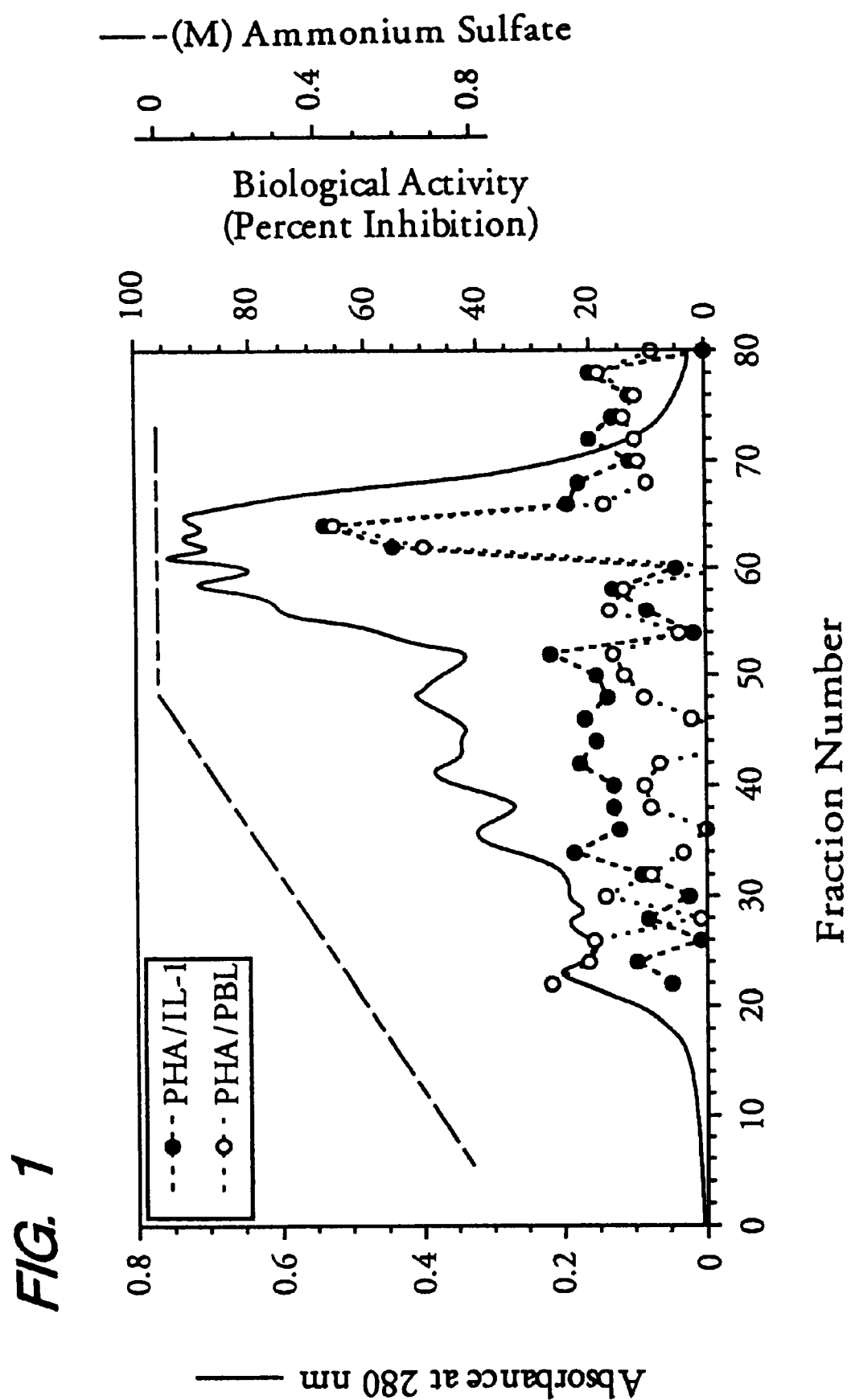
FIG. 1 shows an analytical Phenyl-TSK HPLC chromatographic profile of SK-BR-3 secreted gp97. Inhibition of PHA-stimulated cell proliferation activity was assayed to reveal fractions that contained gp97.

Table 1 shows the effects of anti-gp85–97 antibody on $^3$H-thymidine incorporation by SK-BR-3 cells.

DETAILED DESCRIPTION OF THE INVENTION

The invention described herein is related to previously published work and pending patent applications. By way of example, such work consists of scientific papers, patents or pending patent applications. All of these publications and applications, cited previously or below are hereby incorporated by reference in their entirety.

As used herein, "gp85–97" is defined to mean a class of structurally homologous molecules having lectin-binding properties and biological activities described below. "Structurally homologous" is defined to mean proteins containing substantially identical polypeptide backbones, encoded by the gp85–97 gene and proteolytically processed by cellular enzymes to generate a "mature" N-terminus by removal of the leader sequence. This form of the protein may or may not be further proteolytically nicked, and its amino acid side chains and/or glycosylation sites may also be modified to various extents. The precise chemical structure of gp85–97 depends on a number of factors. Two members of the class are defined as "gp97" and "gp85", which have been isolated from SK-BR-3 cell culture supernatant fluid and human milk, respectively. In their native forms the subunits present in "gp85–97" are understood to occur in a native "complex" of over 1200 kD apparent molecular weight and having a sucrose velocity gradient sedimentation value of about 25S±2S, which operationally defines an apparent native molecular mass of the complex containing gp85–97 subunits.

"Sedimentation value" is defined as the value for gp85–97 extrapolated from the sedimentation behavior of standards of known sedimentation value and molecular weight as analyzed on 5–20% sucrose gradients described in the examples. The sedimentation or S value of a native protein is very reproducible under defined conditions and has been used to estimate the molecular mass of proteins and complexes. Precise determination of the molecular mass of large complexes is known to be difficult and may be influenced by the density and shape of the complex in solution. As ionizable amino and carboxyl groups are present in the molecule, gp85–97 may be obtained as an acidic or basic salt, or in neutral form. All such preparations that retain their activity when placed in suitable environmental conditions are included in the definition of proteins herein. Further, the primary amino acid sequence of the protein may be augmented by derivatization using sugar moieties (glycosylation) or by other supplementary molecules such as lipids, phosphate, acetyl groups and the like, as well as by conjugation with saccharides, polyethylene glycols (PEGs) and polyoxyethylene glycols (POGs). Certain aspects of such augmentation are accomplished through post-translational processing systems of the producing host; other such modifications may be introduced in vitro. In any event, such modifications are included in the definition of gp85–97. It is expected, of course, that such modifications may quantitatively or qualitatively affect the activity, either by enhancing or diminishing the activity of the protein in the various assays. Further, individual amino acid residues in the chain may be modified by oxidation, reduction or other derivatization, and the protein may be cleaved to obtain fragments which retain activity. Certain modifications to the primary structure itself by deletion, addition or substitution of the amino acids incorporated into the sequence during translation can be made without destroying the activity of the protein. Such substitutions which do not destroy activity do not remove the protein sequence from the definition and are considered to have substantially equivalent amino acid sequences. In addition N-terminal and C-terminal deletions and fusions, may be made using known mutagenesis methods.

It is particularly important to appreciate that native gp85–97 is a glycoprotein and that it is difficult to define solely on the basis of its apparent molecular weight on SDS-polyacrylamide electrophoresis (SDS-PAGE). For example, glycosidase treatment of the molecule, as described below, causes a decrease in the molecular weight as revealed by SDS-PAGE. It will thus be further appreciated that gp85–97 isolated from different sources may exhibit different molecular weights when determined by SDS-PAGE, in part as a result of variable glycosylation.

As used herein, "chromatography" is defined to include the application of a solution containing a mixture of compounds to an adsorbent, or other support material which is eluted, usually with a gradient or other sequential eluant. Material eluted from the support matrix is designated the eluate. The sequential elution is most routinely performed by isolating the support matrix in a column and passing the eluting solution(s), which changes affinity for the support matrix, either stepwise or preferably by a gradient, through the matrix. It will be appreciated that encompassed within the definition of "chromatography" is the positioning of the support matrix in a filter and the sequential administering of eluant through the filter, or in a batch-mode.

The phrase "hydrophobic interaction matrix" is defined to mean an adsorbent that is a hydrophobic solid such as polystyrene resin beads, rubber, silica-coated silica gel, or cross-linked agarose sufficiently substituted with hydrophobic functional groups to render the material hydrophobic. Alkyl substituted agarose and aryl substituted agarose such as, for example, phenyl or octyl agarose are representative hydrophobic materials. Mixtures of materials that are chromatographically separated on a hydrophobic interaction chromatography matrix are generally first adsorbed to the matrix in a high salt solution, and subsequently desorbed from the matrix by elution in a low salt solution, or a hydrophobic solvent such as a polyol.

"Anion exchange matrix" is defined to mean a solid or gel support matrix that is charged in aqueous solutions. The support matrix may be agarose sufficiently substituted with amine functional groups to have a net charge in aqueous solutions. The material to be adsorbed is generally bound to the anion exchange matrix in a low salt solution and is generally eluted from the anion exchange matrix in a high-salt eluant containing anions such as chloride ion which bind to the anion exchange matrix and displace the adsorbed material.

By the phrase "high-salt concentration conditions" is meant an aqueous solution wherein an ionic substance is present to create conditions of high ionic strength. Ionic strength is defined as is generally understood in the art and can be calculated from the putative concentrations of the various ions placed in solution, modified by their activity coefficient. High salt concentrations that are routinely employed are typified by solutions containing high concentrations of ammonium sulfate; however, other salts, such as sodium chloride, potassium chloride, sodium sulfate, sodium nitrate, or sodium phosphate may also be employed.

The definition of "affinity chromatography" is understood to be similar to that of Wilchek et al., 1984, *Methods in Enzymology*, 104:3. "Affinity chromatography" is defined as a "method of purification based on biological recognition". Briefly, the procedure involves coupling a ligand to a solid support, and contacting the ligand with a solution containing therein a ligand recognition molecule which binds to the ligand. Subsequently, the ligand recognition molecule is released from the ligand and isolated in pure form. It will be understood that a variety of ligands can be employed in affinity chromatography as discussed by Wilchek, et al., and examples of these include lectins, antibodies, receptor-binding proteins and amino acids.

"Cells" or "recombinant host" or "host cells" are often used interchangeably as will be clear from the context. These terms include the immediate subject cell, and, of course, the progeny thereof. It is understood that not all progeny are exactly identical to the parental cell, due to chance mutations or differences in environment. However, such altered progeny are included when the above terms are used.

The following relates to the antibody aspect of the invention.

"Antibody" as used herein refers to polyclonal, monoclonal and recombinant constructs. Thus, the term includes whole immunoglobin as well as antigen-binding fragments thereof.

The instant invention provides a description of a class of substantially purified molecules, hereinafter referred to as gp85–97, and of DNA sequences that encode members of the class, and materials and methods for identifying and isolating the same. Additionally, vectors for expressing the DNA sequences are also shown. Members of gp85–97, or active fragments derived therefrom, are useful as medicaments for treating or preventing a variety of diseases.

The identification and isolation of the instant gp85–97 DNA sequences were made possible by the design of DNA oligonucleotide probes substantially homologous to the DNA sequences predicted by the protein sequences obtained from gp97. Because such probes were generated based on a knowledge of the partial amino acid sequence of gp97, the order of discussion of the invention will be: methods of assaying for gp85–97; purification of gp97; the partial amino acid sequence of gp97; cloning of the gene encoding gp85–97 using novel gp97 probes; and the identification of gp97 DNA sequences in a cDNA library, along with subcloning; and expression of the sequences.

I. Assay for gp85–97 Activity

One of the properties of gp85–97 is its ability to inhibit the mitogenic response of thymocytes stimulated with phytohaemagglutinin (PHA). Certain other mitogenic lectins, such as ConA, are not measurably inhibited by gp85–97, suggesting significant specificity for PHA. Although PHA apparently stimulates DNA synthesis in a large number of lymphocyte populations (unlike true antigenic stimulation which causes mitogenesis of sub-populations of lymphocytes), the susceptibility of a patient's lymphocytes to PHA stimulation has been shown to correlate with the overall immune responsiveness of the patient. Thus, this assay is widely used to study immune responsiveness.

The procedure for carrying out the phytohaemagglutinin proliferation assay (PHA/PBL) is well known to those skilled in the art. Briefly, it consists of isolating human lymphocytes and incubating an appropriate number of the cells in a suitable physiological solution with an appropriate amount of PHA. Tritiated thymidine is added 48 hours later and allowed to incubate for 24 hours before the cells are washed and counted. Addition of various dilutions of gp85–97 prior to incubation with PHA inhibits stimulation, resulting in less incorporation of radioactive thymidine into DNA, and permitting an estimation of the relative concentration of gp85–97 in the solution being assayed.

A second assay (PHA/IL-1) consists of measuring gp85–97 activity based on its capacity to inhibit IL-2 production from cell lines that are stimulated to produce IL-2 in the presence of PHA and IL-1. A variety of cell lines are known to have this property and the preferred cell line is a murine T-cell line termed LBRM. IL-2 may be measured by several assays, the preferred assay being the enumeration of viable HT-2 cells found after an 18–24 hour period. The HT-2 cell line is a IL-2 dependent mouse helper T-lymphocyte cell line which dies in the absence of IL-2. The assay is described by Gillis et al., 1978, *J. of Immunol.*, 120:2027. Briefly, the proliferation of HT-2 cells in response to IL-2 is measured by a [$^3$H]thymidine ([$^3$H]TdR) incorporation microassay. The HT-2 cells are washed and resuspended at $2 \times 10^5$/ml in RPMI 1640 media containing 10% FBS. Equal volumes of cells and of serial dilutions of recombinant IL-2-containing samples are added to 96-well microtiter plates (Falcon/Becton-Dickinson Labware, Oxnard, Calif. U.S.A.). After 24 hours, incubation cultures were pulsed for 5 hours with 1 $\mu$Ci [$^3$H]TdR (specific activity, 70 Ci/mmol; New England Nuclear, Boston, Mass., U.S.A.), harvested onto Whatman GF/C filters (Whatman Laboratory Products, Inc., Clifton, N.J., U.S.A.), and radioactivity determined in a liquid scintillation counter. IL-2 activity of unknown samples is measured relative to a recombinant human IL-2 standard calibrated in International Units.

Other methods for measuring gp85–97 were based on the ability of native or denatured gp85–97 to bind $^{125}$I-labelled PHA or anti-gp85–97 antibody which was either $^{125}$I-labelled or detected by fluorescence generated by HRP-conjugated goat-anti-rabbit antibody using the ECL kit (Amersham). Approximate concentrations of gp85–97 were determined from autoradiograms of SDS-PAGE blots or non-denatured dot-blot assays probed with the above ligands.

II. Sources of gp85–97

A variety of biological materials are available as sources of gp85–97. Established cell lines may be utilized, and indeed are a preferred source because of the ease with which they can be manipulated and scaled up. For some cell lines, gp85–97 is secreted and thus is present in greatest amounts in the culture medium. For example, gp97 is preferably isolated from SK-BR-3 cell culture media. Thus, culture medium can be the primary source for the molecule. Additional members of gp85–97 may be isolated from other biological sources; for example, human milk is a source of gp85. A PHA-binding protein that reacts with anti-gp85–97 Ab was also detected in supernatants from the A375 human melanoma cell line.

III. Purification of gp85–97

Preferred methods of purifying gp85–97 include various applications of chromatography and separations based on molecular mass, such as sedimentation velocity gradients and size exclusion HPLC. An example of chromatography that effects the separation of molecular structures based on charge differences, and that is employable in the instant invention, is anion exchange chromatography. While a variety of anionic chromatographic materials can be employed, DEAE-Sepharose, obtainable from Pharmacia LKB Biotechnology, Inc., is preferred.

The methods for eluting proteins from anion exchangers are generally well documented in the literature. For example, gp85–97 can be eluted from DEAE using a suitably buffered salt gradient. The nature of the salt and the steepness of the gradient can be determined empirically. Exemplary of an effective salt gradient is sodium chloride varying from about 0–0.8 molar.

A second chromatographic technique, particularly favored in the instant invention, is a form of hydrophobic interaction chromatography. Hydrophobic interaction chromatography (HIC) is generally defined as chromatography which affects separation of proteins based on their hydrophobic properties by binding to alkyl groups, attached to a solid surface, such as Phenyl-TSK HPLC column beads. The proteins can be differentially eluted from the solid surface with a suitable solvent. HIC will generally be employed subsequent to the initial chromatographic step(s), and further purifies gp85–97 by binding gp85–97 and a subset of the contaminating proteins to the hydrophobic matrix in the presence of high salt. The contaminating proteins and gp85–97 are elutable therefrom upon reduction of the salt concentration. The materials and methods for utilizing hydrophobic chromatography are described by Shaltiel S., 1984, *Methods in Enzymology*, 104:69. While it is apparent that there are many hydrophobic chromatographic materials and solid supports that may be employed to purify gp85–97, we have found that Phenyl-TSK is preferred, although phenyl Sepharose is also effective.

Another chromatographic procedure, high performance liquid chromatography, or HPLC, can be applied to enhance the purity of gp85–97. HPLC is related to the third procedure described above in that a preferred version of HPLC as applied to the purification of gp85–97 employs hydrophobic chromatographic material. This method differs from the preceding hydrophobic chromatographic step in at least one aspect: chromatography takes place under high pressure in the presence of an appropriate salt concentration. Examples of the types of materials and methods that can be employed are described by Regnier, F., 1983, *Methods in Enzymology*, 91:137. Preferably employed in the subject invention is chromatographic material having phenyl residues. More preferred are chromatographic materials for preparative and analytical HPLC available from BioRad Corporation that are sold under the name Phenyl-TSK.

In addition to the above described chromatographic techniques, it will be apparent that size-exclusion chromatography, which effects separation of proteins by excluding structures of a predefined size from the chromatographic material employed, while the chromatographic material retains structures of lesser size, may also be employed in the instant invention. Chromatographic materials that are used to construct exclusion columns are widely available and sold under numerous tradenames, an example being the various Sephacryls sold by Pharmacia LKB Biotechnology, Inc. By employing the appropriate chromatographic material, gp85–97 may be separated from other proteins. To obtain gp85–97 in high purity, size exclusion chromatography and/or velocity gradient centrifugation may be combined with ion exchange and hydrophobic chromatography as described above. Sucrose velocity gradient purification is preferred, but other gradients such as glycerol may also be employed.

Regardless of the purification procedures chosen, and depending on the nature of the biological material that gp85–97 is purified from, it is desirable to have present in the various purification solutions one or more protease inhibitors, for example, EDTA, PMSF, and leupeptin. Additionally, as is known in the art, certain purification steps may be conducted at temperatures that reduce the risk of gp85–97 proteolysis.

Western blotting or PHA affinity blotting may be used to monitor the purification of gp85–97 by subjecting preparations containing gp85–97 to sodium dodecyl sulphate polyacrylamide gel electrophoresis under reducing or nonreducing conditions (Laemmli, U., 1970, *Nature*, 227:680–685), and blotting and probing the gels with antibody to gp85–97 or with labelled PHA generally as described by Burnette, 1981, *Anal. Bio. Chem.*, 112:195, or modifications of Burnette's method. Native gp85–97 may also be detected by dot-blotting of undenatured protein and probing with antibody or labelled PHA.

IV. Cloning of gp85–97

A. General Methods:

1) Cloning With Polymerase Chain Reaction

A specific nucleic acid sequence may be cloned into a vector using the polymerase chain reaction (PCR), and primers to amplify the sequence which contains restriction sites on their non-complementary ends. PCR is described in U.S. Pat. No. 4,683,195, issued Jul. 28, 1987, U.S. Pat. No. 4,683,202, issued Jul. 28, 1987 and U.S. Pat. No. 4,800,159, issued Jan. 24, 1989. In general, the synthesis/amplification of DNA sequences by PCR involves an enzymatic chain reaction that produces, in exponential quantities, a specific DNA sequence, provided that the termini of the sequence are known in sufficient detail so that oligonucleotide primers can be synthesized which will hybridize to them, and that a portion of the sequence is available to initiate the chain reaction. The primers are annealed to denatured DNA, followed by extension with a suitable DNA polymerase enzyme, such as the large fragment of DNA polymerase I (Klenow), or preferably a DNA polymerase that is stable in the presence of detergents and nucleotides, which results in newly synthesized plus and minus strands containing the target sequence. Alternatively, a thermostable enzyme present in thermostable bacteria may be used. The enzyme may be produced using DNA recombinant techniques as described in U.S. Ser. No. 063,509, filed Jul. 17, 1987. Because the newly synthesized sequences in the PCR synthetic reaction are also templates for the primers, repeated cycles of denaturing, primer annealing and extension result in exponential accumulation of the region flanked by the primers. PCR thus produces discrete nucleic acid duplexes of cDNA inserts having termini corresponding to the ends of the specific primers employed.

Also useful is the Thermal Cycler instrument (Perkin-Elmer Cetus Instruments) which has been described in European Patent Publication No. 236,069, published Sep. 9, 1987 also incorporated herein by reference in its entirety.

An alternative to the use of plasmid DNAs encoding gp85–97 or fragments thereof as template for PCR is the use of RNA from any cell producing these molecules as template for PCR as described in U.S. Pat. No. 4,800,159. If RNA is the available starting material, the extension product synthesized from one primer, when separated from its complement, can serve as a template for synthesis of the extension product of the other primer. As previously mentioned, each primer contains a restriction site near its 5' end which is the same as or different from the restriction site on the other primer. After sufficient amplification has occurred, the amplification products are treated with the appropriate restriction enzyme(s) to obtain cleaved products in a restriction digest. The desired fragment to be cloned is then isolated and ligated into the appropriate cloning vector.

Although PCR can be performed using a variety of reaction conditions, as described in the references presented above, the preferred reaction conditions are as follows. Plaques that hybridize to a particular probe are eluted into either 0.5 ml of water, or a suitably buffered solution, and 50 $\mu$l of the eluate combined with 10 $\mu$l of 10×PCR buffer, 1.5 $\mu$l of 10 mM dNTP's, 1 $\mu$l of a first and second primer, each at a concentration of about 20 pmoles, 0.2 $\mu$l of Taq polymerase, equivalent to 1 unit of activity. The final volume is 100 $\mu$l. PCR 10×buffer consists of 500 mM KCl, 200 mM Tris-HCl, pH 8.4, 25 mM $MgCl_2$ and 1 mg/ml.

Construction of suitable vectors containing the desired gp85–97 coding sequence employs standard ligation and restriction techniques that are well understood in the art. Isolated vectors, DNA sequences, or synthesized oligonucleotides are cleaved, tailored, and religated in the form desired. A brief description of some of these methods is presented here. General cloning and molecular biology techniques are described by Maniatis et el, T., et al., 1989, *Molecular Cloning*, Cold Spring Harbor Lab., Cold Spring Harbor, N.Y., volumes 1 and 2.

Site-specific DNA cleavage is performed by treating the DNA with suitable restriction enzyme(s) under conditions that are generally understood in the art, and the particulars of which are specified by the manufacturer of these commercially available restriction enzymes. See, e.g., New England Biolabs, Product Catalog. In general, about 1 $\mu$g of plasmid or DNA sequence is cleaved by 1 unit of enzyme in about 20 $\mu$l of buffer solution. In the examples herein, typically, an excess of restriction enzyme is used to ensure complete digestion of the DNA substrate. Incubation times of about 1 to 2 hours at about 37° C. are workable, although variations can be tolerated After each incubation, protein is removed by extraction with phenol/chloroform, and may be followed by ether extraction, and the nucleic acid recovered from aqueous fractions by precipitation with ethanol, followed by chromatography using a Sephadex G-50 spin column. If desired, size separation of the cleaved fragments may be performed by polyacrylamide gel or agarose gel electrophoresis using standard techniques. A general description of size separations is found in *Methods in Enzymology*, 65:499–560 (1980).

Restriction fragments may be blunt-ended by treating with a large fragment of *E. coli* DNA polymerase I that is known as the Klenow fragment in the presence of the four deoxynucleotide triphosphates (dNTPs) using incubation times of about 15 to 25 minutes at 20 to 25° C. in 50 mM Tris pH 7.6, 50 mM NaCl, 6 mM $MgCl_2$, 6 mM DTT and 10 mM dNTPs. After treatment with Klenow, the mixture is extracted with phenol/chloroform and ethanol precipitated. Treatment under appropriate conditions with S1 nuclease may also be used to hydrolyze single-stranded portions.

Ligations are generally performed in 15–30 $\mu$l volumes under the following standard conditions and temperatures: 20 mM Tris-Cl pH 7.5, 10 mM $MgCl_2$, 10 mM DTT, 33 $\mu$g/ml BSA, 10 mM–50 mM NaCl, and either 1–40 $\mu$M, ATP, 0.01–0.02 (Weiss) units T4 DNA ligase at 0° C. for "sticky end" ligation, or for "blunt-end" ligations 1 mM ATP and 0.3–0.6 (Weiss) units T4 ligase at 14° C. Intermolecular "sticky end" ligations are usually performed at 33–100 $\mu$g/ml total DNA concentration. In blunt-end ligations, the total DNA concentration of the ends is about 1 $\mu$M.

In vector construction employing "vector fragments", the vector fragment is commonly treated with bacterial alkaline phosphatase (BAP) in order to remove the 5' phosphate and prevent religation of the vector. BAP digestions are conducted at pH 8 in approximately 150 mM Tris, in the presence of $Na^+$ and $Mg^{+2}$ using about 1 unit of BAP per $\mu$g of vector at 60° C. for about 1 hour. Nucleic acid fragments are recovered by extracting the preparation with phenol/chloroform, followed by ethanol precipitation. Alternatively, religation can be prevented in vectors which have been double digested by additional restriction enzyme digestion of the unwanted fragments.

In the constructions set forth below, correct ligations are confirmed by first transforming the appropriate *E. coli* strain with the ligation mixture. Successful transformants are selected by resistance to ampicillin, tetracycline or other antibiotics, or using other markers depending on the mode of plasmid construction, as is understood in the art. Miniprep DNA can be prepared from the transformants by the method of D. Ish-Howowicz et al., 1981, *Nucleic Acids Res*, 2:2989 and analyzed by restriction and/or sequenced by the dideoxy method of F. Sanger et al., 1977, *PNAS* (*USA*), 74:5463 as further described by Messing et al., 1981, *Nucleic Acids Res.*, 9:309, or by the method of Maxam et al., 1980, *Methods in Enzymology*, 65:499.

Host strains used in cloning in M13 consist of *E. coli* strains susceptible to phage infection, such as *E. coli* K12 strain DG98. The DG98 strain was deposited with ATCC, on Jul. 13, 1984 and has Accession No. 1965.

Transformation is done using standard techniques appropriate to the chosen host cells. The calcium treatment employing chloride, as described by S. N. Cohen, 1972, *PNAS* (*USA*), 69:21 10, or the $RbCl_2$ method described in Maniatis et al., 1982, *Molecular Cloning: A Laboratory Manual*, Cold Spring Harbor Press, p.254 may be used for procaryotes. Transfection of insect cells, such as for example, Sf9 cells, may be achieved using a modification of the calcium phosphate precipitation technique (Graham, F. L. et al., 1973, *Virology*, 52:456) as adapted for insect cells,(J. P. Burandetal., 1980, *Virology*, 101; E. B. Casstens etal., 1980, *Virology*, 101:311).

B. Oligonucleotide Synthesis:

Synthetic oligonucleotides may be prepared by the triester method of Matteucci et al., 1981, *J. Am Chem. Soc.*, 103:3185 or using commercially available automated oligonucleotide synthesizers. Kinasing of single strands prior to annealing or for labeling is achieved using an excess, e.g., approximately 10 units of polynucleotide kinase to 0.1 nmole substrate in the presence of 50 mM Tris, pH 7.6, 10 mM $MgCl_2$, 5 mM dithiothreitol, 1–2 mM ATP, 1.7 pmoles$\lambda^{32}$P-ATP (2.9 mCi/mmole), 0.1 mM spermidine, 0.1 mM EDTA.

Using the partial N-terminal and internal gp85–97 amino acid sequences described below, and known codon redundancies thereto, DNA oligonucleotides were synthesized and used as probes for probing cDNA libraries for sequences that encode gp85–97, or as primers for conducting PCR reactions, discussed below.

C. Identification and Isolation of gp85–97 DNA Sequences:

Several procedures are available that may be suitable for identifying gp85–97 DNA sequences. One procedure is to use the oligonucleotide probes identified and synthesized as described above to screen cDNA libraries. cDNA libraries can be constructed using techniques known in the art, or can be purchased commercially.

An illustrative procedure for making a cDNA library containing gp85–97 sequences may consist of isolating total cytoplasmic RNA from a suitable starting material, and further isolating messenger RNA therefrom. The latter can be further fractionated into Poly (A+) messenger RNA, which in turn is fractionated further still into Poly (A+) messenger RNA fractions containing gp85–97 messenger RNA. The appropriate gp85–97 messenger RNA can then be reverse transcribed and cloned into a suitable vector to form the cDNA library.

More specifically, the starting material (i.e., tissue, cells) is washed with phosphate buffered saline, and a non-ionic detergent, such as a polymer of ethylene oxide. For example, NP-40 is added in an amount to lyse the cellular membranes preferentially, generally about 0.3%. Nuclei can then be removed by centrifugation at 1,000×for 10 minutes. The post-nuclear supernatant is added to an equal volume of TE (10 mM Tris, 1 mM ethylenediaminetetraacetic acid (EDTA), pH 7.5) saturated phenol/chloroform (1:1) containing 0.5% sodium dodecyl sulfate (SDS) and 10 mM EDTA. The supernatant is re-extracted 4 times and phase separated by centrifugation at 2,000×g for 120 minutes. The RNA is precipitated by adjusting the samples to 0.25 M NaCl, adding 2 volumes of 100% ethanol and storing at −20° C. The RNA is then pelleted at 5,000×g for 30 minutes, washed with 70% and 100% ethanol, and dried. This represents the total cytoplasmic RNA. Polyadenylated (Poly A+) messenger RNA (mRNA) can be obtained from the total cytoplasmic RNA by chromatography on oligo (dT) cellulose (J. Aviv et al., 1972, *PNAS*, 69:1408–1412). The RNA is dissolved in ETS (10 mM Tris, 1 mM EDTA, 0.5% SDS, pH 7.5) at a concentration of 2 mg/ml. This solution is heated to 65° C. for 5 minutes, then quickly chilled to 4° C. After bringing the RNA solution to room temperature, it is adjusted to 0.4 M NaCl and slowly passed through an oligo (dT) cellulose column previously equilibrated with binding buffer (500 mM NaCl, 10 mM Tris, 1 mM EDTA, pH 7.5). The flow-through is passed over the column twice more, and the column washed with 10 volumes of binding buffer. Poly (A+) mRNA is eluted with aliquots of ETS, extracted once with TE-saturated phenol chloroform and precipitated by the addition of NaCl to 0.2 M and 2 volumes of 100% ethanol. The RNA is reprecipitated twice, washed once in 70% and then 100% ethanol prior to drying. The poly (A+) mRNA can then be used to construct a cDNA library.

cDNA can be made from the enriched mRNA fraction using oligo (dT) priming of the poly A tails and AMV reverse transcriptase employing the method of Okayama, H., et al., 1983, *Mol. Cell Biol.*, 3:280, incorporated herein by reference.

Other methods of preparing cDNA libraries are, of course, well known in the art. One method uses oligo (dT) primer, reverse transcriptase, tailing of the double stranded cDNA with poly (dG) and annealing into a suitable vector, such as pBR322 or a derivative thereof, which has been cleaved at the desired restriction site and tailed with poly (dC). A detailed description of this alternative method is found, for example, in U.S. Ser. No. 564,224, filed Dec. 20, 1983, and assigned to the same assignee, incorporated herein by reference. Indeed, this method is preferred and was used to create a cDNA library from the THP-1 cell line using the vector pCDL-SRα296 to identify and isolate gp85–97 DNA sequences.

A preferred cDNA library would be made applying the methods described above and using mRNA from the human monocytic leukemia cell line, THP-1 (Dr. Tsuchiga at Res. Inst. for Tuberculosis and Cancer, Tohoku Univ. Japan).

Most preferred is to construct a cDNA library using mRNA isolated from mezerin-treated THP-1 cells, and the vector pCDL SRα-296. pCDLSRα-296 may be obtained from DNAX Corporation, and is described by Takebe et al., 1988, *Molecular and Cellular Biology*, 8(1):466; and in U.S. Pat. No. 4,695,542.

Finally, as mentioned above, cDNA libraries are commercially available, and can be purchased and used to identify and isolate the desired gp85–97 DNA sequences. A particularly useful library is sold by Clontech (Catalog number #L H1008). It is a λ gt11 human placental cDNA library made from total poly (A+) messenger RNA.

V. Antibody to gp85–97

Polyclonal, monoclonal, or recombinant antibodies to gp85–97 may be produced using various techniques. The antibody is preferably human or humanized, although non-human antibody will perform satisfactory. The preparation of high-titer neutralizing polyclonal antibody can be realized by immunizing a variety of species and employing one of several different immunization regimes. The preferred method of the instant invention is to immunize rabbits with gp85–97 prepared in complete Freund's adjuvant. A native complex containing either the 85–97 kD molecule and/or fragments derived therefrom may be utilized as immunogen. The animals are subsequently subjected to multiple boosts (containing about half the original amount of the appropriate molecule) in incomplete Freund's adjuvant at about 21-day intervals. About 10 days following each 21-day interval, 20–30 ml of blood is removed, the serum isolated and antibody isolated therefrom. This procedure may be carried out for a period of several months.

Monoclonal antibody may be produced using native gp85–97 complex, its subunit, or fragments derived therefrom as immunogen, and using the procedures described by Kohler, G. and Milstein, C., 1975, *Nature*, 256:495, or modifications thereof that are known in the art.

The work of Kohler and Milstein, above, involves fusing murine lymphocytes and drug selectable plasmacytomas to produce hybridomas. A suitable plasmacytoma is Sp 2/0-Ag14 and is widely used by practitioners of this art. Subsequent to the work of Kohler and Milstein, the hybridoma technique has been applied to produce hybrid cell lines that secrete human monoclonal antibodies. The latter procedures are generally described in Abrams, P., 1986, *Methods in Enzymology*, 121:107, but other modifications are known to those skilled in the art.

Regardless of whether murine or human antibody is produced, the antibody-secreting cells are combined with the fusion partner and the cells fused with a suitable fusing agent, preferably polyethylene glycol, and more preferably polyethylene glycol 1000. The latter is added to a cell pellet containing the antibody-secreting cells and the fusion partner in small amounts over a short period of time accompanied with gentle agitation. After the addition of the fusing agent, the cell mixture is washed to remove the fusing agent and cellular debris, and the cell mixture consisting of fused and unfused cells seeded into appropriate cell culture chambers containing selective growth media. After a period of several weeks, hybrid cells are apparent, and may be screened for appropriate antibody production and subcloned to ensure the availability of a stable hybrid cell line. Cells may also be fused using electrofusion techniques as is known in the art.

The preferred antibody is human monoclonal antibody which can be prepared from lymphocytes sensitized with gp85–97 material, either in vivo or in vitro by immortalization of antibody-producing hybrid cell lines, thereby making available a permanent source of the desired antibody, using the cell fusion techniques described above. Alternatively, sensitized lymphocytes may be immortalized by a combination of two techniques, viral transformation and cell fusion. The preferred combination consist of transforming antibody-secreting cells with Epstein-Barr virus, and subsequently fusing the transformed cells to a suitable fusion partner. Such fusion partners are known in the art, and exemplary partners may be a mouse myeloma cell line, a heteromyeloma line, or a human myeloma line, or other immortalized cell line. PCT Patent Application No. 81/00957; Schlom et al., 1980, *PNAS USA*, 77:6841; Croce et al., 1980, *Nature*, 288:488. The preferred fusion partner is a mouse-human hetero-hybrid, and more preferred is the cell line designated F3B6. This cell line is on deposit with the American Type Culture Collection, Accession No. HB8785. It was deposited Apr. 18, 1985. The procedures for generating F3B6 are described in European Patent Application, Publication No. 174,204. Techniques applicable to the use of Epstein-Barr virus transformation and the production of immortal antibody secreting cell lines are presented by Roder, J. et al., 1986, *Methods in Enzymology*, 121:140.

It will be apparent to those skilled in the art, and as mentioned above, while the preferred embodiment of the instant invention is neutralizing gp85–97 monoclonal antibody, such antibody(s) may be altered and still maintain biological activity. Thus, encompassed within the scope of the invention is antibody modified by reduction to various size fragments, such as $F(ab')_2$, Fab, Fv, or the like. Also, the hybrid cell lines that produce the antibody may be considered to be a source of the DNA that encodes the desired antibody, which may be isolated and transferred to cells by known genetic techniques to produce genetically engineered antibody. An example of the latter would be the production of single chain antibody having the antibody combining site of the hybridomas described herein. Single chain antibody is described in U.S. Pat. No. 4,704,692.

A second example of genetically engineered antibody is recombinant, or chimeric antibody. Methods for producing recombinant antibody are shown in U.S. Pat. No. 4,816,567, to Cabilly, et al.; Japanese patent application, Serial No. 84-169370, filed Aug. 15, 1984; U.S. Ser. No. 644,473, filed Aug. 27, 1984; British patent application 8422238, filed on Sep. 3, 1984; Japanese patent application, No. 85-239543, filed Oct. 28, 1985; U.S. Ser. No. 793,980 on Nov. 1, 1985; U.S. Ser. No. 77,528, filed Jul. 24, 1987. Also, British patent application, No. 867679, filed Mar. 27, 1986, describes methods for producing an altered antibody in which at least parts of the complementary determining regions (CDRs) in the light or heavy chain variable domains have been replaced by analogous parts of CDRs from an antibody of different specificity. Using the procedures described therein it is feasible to construct recombinant antibody having the CDR region of one species grafted onto antibody from a second species that has its CDR region replaced.

Having described what the applicants believe their invention to be, the following examples relating to gp85 and gp97 isolated from human milk and SK-BR-3 cells, respectively, are presented to illustrate the invention and are not to be construed as limiting the scope of the invention. For example, variation in the source, type, or methods may be employed without departing from the scope of the present invention.

EXAMPLE 1

Assays/Purification/Characterization of SK-BR-3 gp97

I. Assays for gp85–97

A. Proliferation Assays

Activity of gp85–97 was measured using one of two PHA-stimulated cellular assays. Human peripheral blood mononuclear cells were isolated from freshly heparinized blood by density centrifugation using Ficoll-Hypaque (Pharmacia LKB Biotechnology Inc.). Mononuclear cells were isolated from the interface, washed three times in Roswell Park Memorial Institute 1640 (RPMI 1640) media supplemented with 1% L-glutamine, penicillin (100 units/ml), streptomycin (100 $\mu$g/ml), and the resulting cells resuspended in media used to perform the assay.

The mononuclear cells were resuspended in a concentration of $0.67 \times 10^6$ cell/ml in assay mixture containing the following: RPMI 1640 media containing 25 mM Hepes, 10% heat-inactivated fetal calf serum, 1% L-glutarnine, and 2% penicillin (200 units/ml) and streptomycin (200 $\mu$g/ml).

Next, 150 $\mu$l of mononuclear cell suspension containing PHA (0.25 $\mu$g/ml) were added to wells in a 96-well U-bottom tissue culture plate (Costar). This suspension contained $1 \times 10^5$ cell/well. This mixture was added to wells that contained either 50 $\mu$l of sample being assayed for gp85–97 activity, or 50 $\mu$l of control buffer.

The 96-well plates were incubated for 3 days at 37° C. in a tissue culture incubator. Eighteen hours prior to completing the assay, the cell cultures were labelled with 0.5 uCi/well of $^3$H-thymidine (2 Ci/mmole). After the 18-hour radiolabelling period, cells from the 96-well plates were harvested with an automatic cell harvester (Skatron, Inc., Sterling, Va.) and processed for liquid scintillation counting. Incorporation of $^3$H-thymidine into DNA was measured using a LKB beta plate scintillation counter (Pharmacia LKB Biotechnology, Inc.). The data shown in the figures is expressed as percent inhibition of proliferation as compared to control cells treated with medium containing control buffer.

In addition to the proliferation assay described above, gp85–97 activity was assayed by measuring the capacity of the molecule to inhibit IL-2 production from LBRM-33 cells. In the presence of PHA and IL-1 this cell line secretes IL-2, which can be assayed on HT-2 cells that require IL-2 for proliferation.

The assay was conducted in 96-well tissue culture plates (Falcon Corp., 3072). Chromatographic fractions sought to be tested for gp85–97 activity were dialyzed into PBS and diluted into assay media consisting of RPMI 1640 supplemented with 10% fetal calf serum and $5 \times 10^5$ M $\beta$-mercaptoethanol. The final volume was 50 $\mu$l/well. Plates were sterilized by U.V. irradiation prior to assay. Next, LBRM-33 cells were diluted in the above-described assay media at $5 \times 10^5$ per ml, and PHA-L (Sigma L-4144) added to a final concentration of 2.5 $\mu$g/ml. 100 $\mu$l/well of LBRM-33 cells were added into the samples being tested for gp97 activity. This mixture was incubated for 1 hour at 37° C. prior to adding IL-1. At the end of the 1-hour incubation period, 50 $\mu$l/well of IL-1 was added to each well to a final concentration of 0.08 units/ml. The IL-1 was made up in assay media at a concentration 0.312 units/ml. Control samples that did not receive IL-1 received 50 $\mu$l/well of assay media only. The final concentration of IL-1 in the wells was 0.08 units/ml. Controls include wells with LBRM-33 cells that did not receive PHA and wells that lacked both LBRM-33 cells and PHA.

Wells were then incubated at 37° C. for 18–24 hours in a tissue culture incubator. Cells were pelleted by centrifuging the plates at 1,000 rpm for 10 minutes, and the top 50 $\mu$l of supernatant of each well was transferred into a new well. HT-2 cells were made up to a concentration of $2 \times 10^5$ cell/ml in assay media, and 50 $\mu$l of this was added per well that contained the 50 $\mu$l of supernatant. The HT-2 cells were incubated for 18–24 hours at 37° C., and pulsed with 1 uCi/well of $^3$H-thymidine (50 $\mu$l/well, NEN No. NET-027A) for 3–4 hours. The wells were harvested with an automated cell harvester and processed for liquid scintillation counting.

B. Western and Affinity Blotting:

Western blotting, or PHA affinity blotting was used to monitor the purification of gp85–97 and consists of subjecting preparations containing the molecule to sodium dodecyl sulphate (SDS) polyacrylamide gel electrophoresis under reducing, or "nonreduced" conditions (Laemmli, U., 1970, *Nature*, 227:680–685), and blotting and probing the blots with antibody to gp85–97 or labelled PHA generally as described by Burnette, 1981, *Anal. Bio. Chem.*, 112:195, or modifications of Burnette's method. Samples were blotted onto 0.45 $\mu$m Immobilon P (Millipore), blocked with Western buffer consisting of 3 mM KCl, 0.14 M CaCl, 1.5 mM $K_2HPO_4$, 8 mM $NaH_2PO_4$, pH 7.4 (PBS), to which 0.02% azide, 0.1% bovine serum albumin, 0.1% ovalbumin and 0.1% Tween 20 were added, probed with $^{125}$I-PHA-L (labelled using Pierce Iodo-Beads), washed, and counted with a multi-wire proportional detector (automated Microbiology Systems, Inc.).

In some cases the concentration of gp85–97 was also determined by serially diluting fractions, dot-blotting onto polyvinylidene difluoride paper, probing with anti-gp85–97 Ab, and quantitative scanning of autoradiograms standardized to dilutions of gp97. Densitometric measurements were performed using an Apple Macintosh II computer and 16-bit Apple scanner with an Abaton Scan program. Autoradiograms of a selected dot-blot dilution were scanned, and relative gp85–97 concentration was determined from the product of the size of the dot times the average density of the dot using an Image 1.3.5 program. Absolute gp85–97 concentrations could then be determined from scans of dilutions of known amounts of purified gp85–97 on the same autoradiogram.

For anti-gp85–97 antibody dot blots, polyclonal rabbit antibody against purified native gp97 was prepared by Berkeley Antibody Company and purified by protein A Sepharose chromatography, followed by affinity chromatography using 97 and 70 kDa SK-BR-3 gp97 subunits (purified by high-performance electrophoretic chromatography) coupled to BioRad Affigel 10/15 and eluted with 0.1 M glycine at pH 2. gp85–97 concentration was determined by dot-blotting serially diluted samples, blocking (as above), probing with $^{125}$I-labelled anti-gp85–97 antibody, and performing quantitative densitometry on autoradiograms.

N-terminal gas phase sequencing of gp85–97 can be performed following SDS-PAGE of purified material and transfer to PVDF membrane. Internal amino acid sequences can be obtained after digestion of gp85–97 with an appropriate enzyme, for example Lys-C protease, followed by SDS-PAGE and transfer onto PVDF membrane and sequencing using an ABI gas phase sequencer.

II. Purification of gp97

10 liters of SK-BR-3 cell culture supernatant were used as a source of purification of gp97. Cells were grown in serum-free and insulin-free DMEM media for 3 days prior to collecting the media.

The conditioned medium was adjusted to contain various protease inhibitors, including 1 mM EDTA, 1 μg/ml leupeptin, and 200 μM PMSF. These inhibitors at these concentrations were used in all buffers throughout the purification.

The conditioned media was concentrated 20-fold with an Amicon YM10 Spiral Cartridge concentrator. The retentate was dialyzed into 25 mM Tris buffer, pH 8.5, and chromatographed over a DEAE-Sepharose (Pharmacia) column having the dimensions of 5×20 cm. The protein was eluted with a 0–0.7 M gradient of sodium chloride delivered at a rate of 10 ml/minute with a total volume of 1.5 liters. Those fractions enriched in gp97 were pooled and were made 0.8 M in ammonium sulphate, pH 7.0, prior to initiating the next chromatographic procedure.

Three aliquots each containing a total of 150 mg of protein from the DEAE-Sepharose pooled fractions were separately applied to a BioRad preparative phenyl-TSK HPLC column, having the dimensions 21.5×150 mm. Protein was eluted from the column at 3 ml/min with a crisscrossing gradient of decreasing ammonium sulphate (starting at 0.8 M) and increasing ethylene glycol from 0–30%. Each of the three DEAE-Sepharose aliquots was treated in this manner and yielded a single peak of gp97 following the Phenyl-TSK column. A representative example of Phenyl-TSK chromatography at this stage of the purification is shown in FIG. 1. These Phenyl-TSK column fractions were pooled, dialyzed into phosphate buffered saline and concentrated approximately 20-fold with an Amicon stir cell using a YM10 membrane.

Figure 2A:
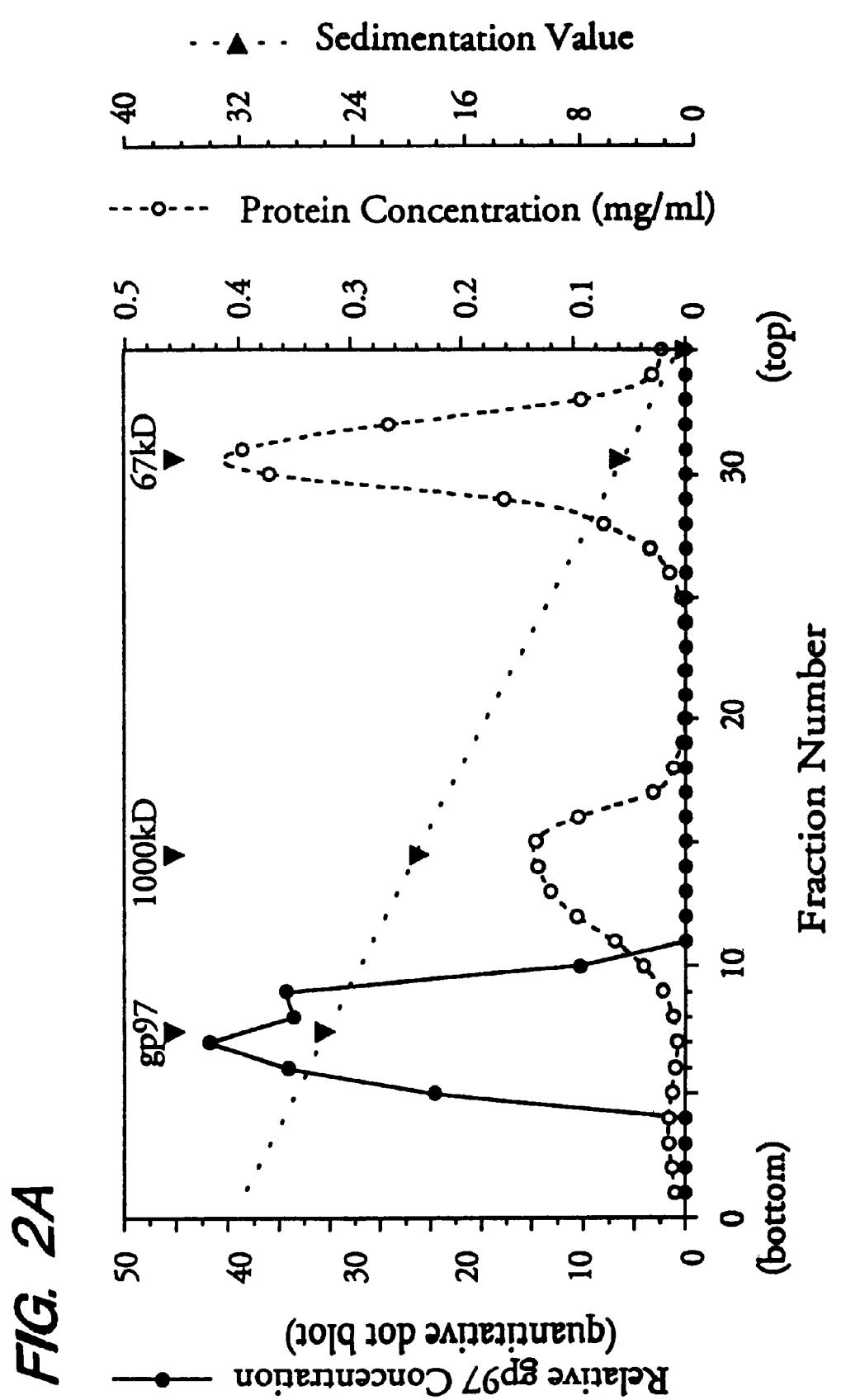
FIG. 2A shows a sucrose gradient centrifugation profile of purified SK-BR-3 gp97 as detected using a non-denaturing dot-blot assay with anti-gp 85–97 antibody.

Next, 2 ml aliquots of the concentrated material were layered on a 37 ml, 5–50% sucrose gradient buffered with phosphate-buffered saline and centrifuged in a Beckman SW28 rotor at 24,000 rpm at 10° C. for 39 hours. The bottom of the tube was punctured, and fractions collected therefrom FIG. 2A. The purified gp97 was dialyzed into phosphate-buffered saline without protease inhibitors, filter-sterilized using a 0.45 μm acrodisc filter (Gelman Sciences), and stored at 4° C. Starting with the 3-day conditioned medium from SK-BR-3 cells, the purification protocol yielded 3.3 mg of gp97, a fraction of which had been cleaved into 70 kD and 27 kD fragments FIG. 2B. This corresponds to a 300-fold purification with a 20% recovery.

Purified gp97 protein from an essentially identical purification was dialyzed against PBS, concentrated by Amicon YM30 ultrafiltration to 0.5 mg/ml and run on an 8% reducing SDS-PAGE that had been pre-electrophoresed in 0.1 M Tris pH 8.9 and 0.1% SDS and 0.1 mM thioglycolate for 1 hour and then returned to gel running buffer (containing 0.1 mM thioglycolate) for sample separation. Protein bands were transferred to a PVDF membrane (Pro-Blot, Applied Biosystems, Inc.) and visualized by brief Coomassie Blue staining. A predominant 70 kD band was detected and subsequently sequenced using a gas phase sequencer (Applied Biosystems). The following N-terminal sequence was obtained: VNDGDM?LAD. A 97 kD molecular weight band was also sequenced from a third, essentially identical, gp97 preparation. The following N-terminal sequence was obtained: (SEQ ID NO:1).

A. Characterization:

The apparent native molecular weight of the purified SK-BR-3 complex was estimated by sedimentation velocity analysis using 12 ml, 5–20% sucrose (w/v) gradients in phosphate-buffered saline (PBS) containing 2.5 mM EDTA, 0.2 mM phenylmethysulfonyl fluoride, and 2 μg/ml leupeptin. Purified SK-BK-3 gp97 (6 μg) was mixed with 0.2 mg bovine serum albumin in a total of 200 μl of PBS and centrifuged in a SW40 rotor at 28 K rpm at 15° C. for 16 hours. Fractions were collected from the bottom and assayed for marker protein by BioRad assay (read at 595 nm). A control gradient containing 400 μg BSA and 600 μg IgM T88 in 200 μl PBS was also run in parallel. The gp97 peak was located by rabbit anti-gp85–97/goat anti-rabbit HRP antibody detection of 10 μl of each fraction, serially diluted and dot-blotted onto PVDF membrane and visualized by fluorescence FIG. 2A. Autoradiograms were scanned to quantitate relative gp97 concentration and determine the position of the peak. The sedimentation coefficient of macromolecules has been used to determine native moleuclar weights. The S value of gp97 is approximately 25.

Figure 3:
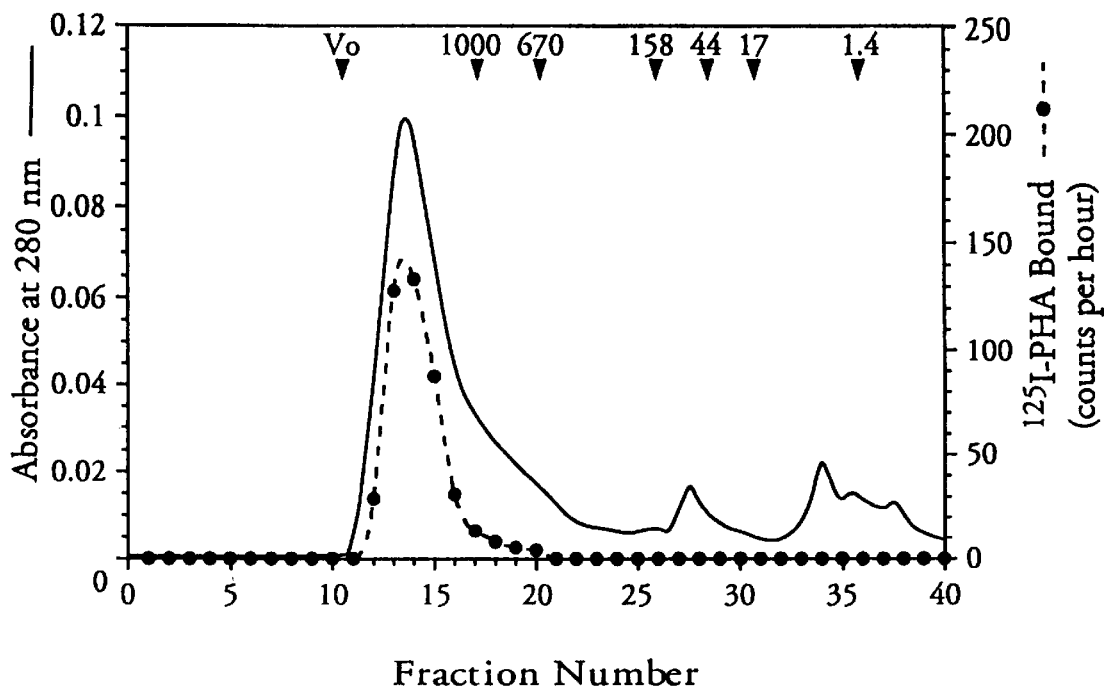
FIG. 3 shows the apparent native molecular mass of gp97 complexes isolated from SK-BR-3 cells determined via chromatography on a Sepharose 6 size exclusion HPLC column.

The apparent native molecular mass of the gp97 isolated from SK-BR-3 cell culture supernatants was also estimated by chromatography on a Sepharose 6 size exclusion HPLC column (Pharmacia) using phosphate buffered saline, 0.5 ml/minute, as the mobile phase. FIG. 3 shows the results. Fractions containing gp97 were identified using the $^{125}$I-PHA dot blot assay as described above. The apparent native molecular weight is larger than the largest standard, IgM T88, and is estimated to be over 1200 kD. The hybridoma that secretes the IgM T88 monoclonal antibody is on deposit with the American Type Culture Collection with Accession No. HB7431.

The density of purified SK-BR-3 gp97 complex was measured by equilibrium density centrifugation, wherein 30 μg of gp97 was mixed into 14 ml of phosphate-buffered saline solution containing CsCl at a density of 1.35 gm/ml. This mixture was centrifuged in a Beckman SW40 rotor at 28,000 rpm at 5° C. for 70 hours. The bottom of the tube-was punctured, 0.5 ml fractions collected, and the density of each fraction determined by weighing aliquots of the fractions in triplicate in sealed tubes. It was determined that the density of purified SK-BR-3 gp97 is approximately 1.35 gm/ml.

Figure 4A:
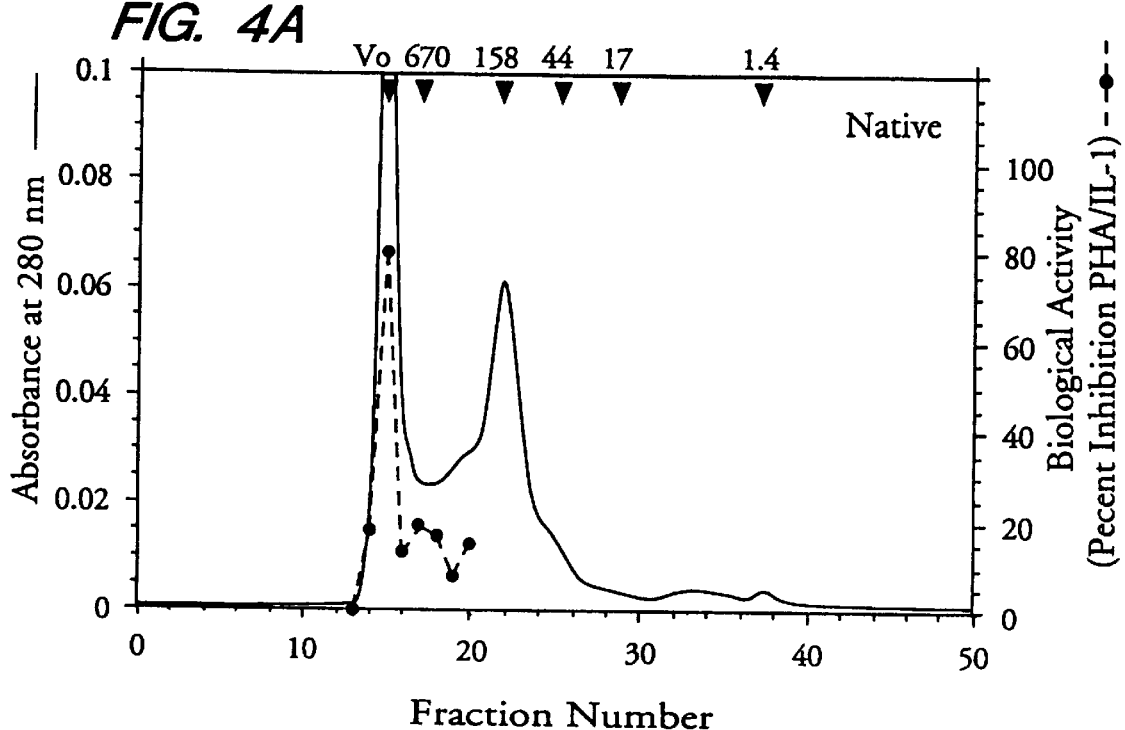
FIG. 4 shows a Bio-Sil SEC 250 size exclusion HPLC chromatographic profile of partially purified SK-BR-3 gp97 in native form (4A) or after trypsin digestion (4B).
Figure 4B:
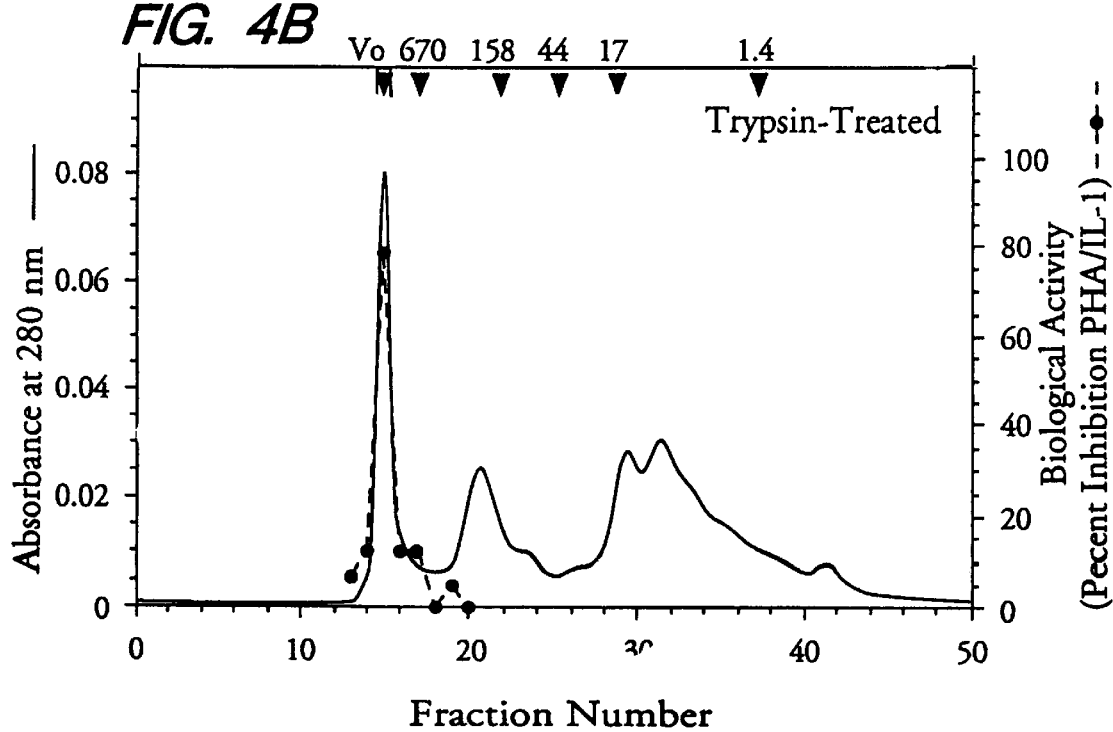

An experiment was done to determine the sensitivity of partially purified gp97 to trypsin digestion. The gp97 native complex was treated with trypsin at a ratio of 1:10 (w/w trypsin to total protein), for 60 minutes at 37° C. FIG. 4 shows a Bio-Sil SEC-250 size exclusion-HPLC chromatographic profile of the material before and after digestion. SDS-PAGE of these two preparations revealed that the semi-purified gp97 was relatively protease-resistant (following limited digestion with trypsin) into 70 kD and 27 kD fragments, while other bands were much more extensively degraded. The N-terminal sequence of the 70 kD band (following transfer to PVDF membrane) corresponded to that of the purified SK-BR-3 gp97 described above.

Lectin-binding studies were carried out on gp97 (containing 70 kD and 27 kD fragments) to partially characterize the sugar components of the glycoprotein. The reported sugar specificities of the lectins used are as follows: 1) con A ((α-D-mannose and α-D-glucosamine), 2) lentil lectin ((α-D-mannose), 3) wheat germ agglutinin [(D-glcNAc)$_2$ and NeuNAc], and 4) phytohemagglutinin, leukocyte-specific (oligosaccharides). Purified gp97 (50 ng in 300 μl of PBS) was incubated 2 hours at room temperature with shaking with various lectins immobilized on various agarose beads (25 μl of beads per incubation). After removal of the beads by centrifugation, residual unbound gp97 in the supernatant was measured by the anti-gp85–97 antibody dot-blot assay described above. Only PHA-L and wheat germ agglutinin bound gp97 in significant amounts.

Similar studies were done using $^{125}$I-labelled PHA-L binding to gp97 run on SDS-PAGE and blotted onto PVDF paper. The effect of pretreatment with glycosidases was also studied in this system to partially characterize the linkage of the sugars in gp97. Each glycosidase reaction was carried out on 6 micrograms of purified gp97 that had been denatured by boiling for 5 minutes in 0.1% sodium dodecyl sulphate containing 2-mercaptoethanol in 100 mM Hepes at pH 7.0. NP40 was added to a final concentration of 1% (w/v), and individual 60 microliter reactions were incubated for 18 hours at 37° C. after addition of the following units of enzyme: 1) 2 milliunits of neuraminidase (Boehringer Mannheim Biochemicals); 2) 2 milliunits of neuraminidase, plus 1 milliunit of O-glycan-peptide-hydrolase (Boehringer Mannheim); and 3) 0.5 milliunits of N-glycanase (Genzyme). CaCl$_2$ was added to 4 mM in reactions containing neuraminidase. SDS-PAGE was performed in triplicate on 20 microliter aliquots of each reaction, including control reactions. Products were visualized by each of the following methods: 1) Coomassie Blue staining; 2) blotting and probing with the anti-SK-BR-3 gp97 antibody followed by $^{125}$I-protein A; and 3) blotting and probing with $^{125}$I-PHA.

All three detection methods revealed changes in the molecular weight of the molecule on SDS-PAGE following glycosidase treatment. Neuraminidase treatment caused a small shift, implying the presence of sialic acid. O-glycan-peptide-hydrolase treatment had no additional effect, suggesting the absence of significant O-glycosylation. N-glycanase treatment resulted in a large shift in molecular weight suggesting the presence of significant N-linked glycosylation. $^{125}$I-PHA was observed to bind all antibody-reactive bands except material treated with N-glycanase, suggesting that the PHA-L binds to a N-linked sugar component of gp97.

EXAMPLE 2

Cloning of the Gene Encoding Human gp97

The gene encoding human gp85–97 was cloned using the following general strategy. First, SK-BR-3 gp97 which had been recovered in partially proteolyzed form, was denatured and reduced, and the 97 kD and 70 kD molecules were purified using size exclusion HPLC in 0.1% SDS. The 97 kD and 70 kD molecules were digested with Lys-C protease, and the resulting peptides purified and sequenced. Next, based on the amino acid sequence of one of the peptides, peptide I, degenerate oligonucleotide primers were synthesized and used in a PCR reaction on SK-BR-3 mRNA which yielded DNA sequences that were, in turn, used to synthesize other oligonucleotide primers that eventually lead to the synthesis of a specific DNA probe for screening a cDNA library to obtain the full-length cDNA sequence that encodes SK-BR-3 gp97.

More specifically, 1 mg of partially proteolyzed SK-BR-3 gp97 was denatured in 2% sodium dodecyl sulphate and reduced with 40 mM dithiothreitol. The mixture was heated to 50° C. for 10 minutes and chromatographed on a Pharmacia Superose 6 size exclusion-HPLC column using a mobile phase of 0.1% sodium dodecyl sulphate in 25 mM Tris (pH 8.5) containing 1 mM EDTA flowing at a rate of 0.6 ml/minute. The purified 97 kD subunit and 70 kD fragment were separately treated with 5% (w/w) Lys-C protease at 37° C. for 18 hours. To determine the extent of digestion and the peptides produced, one third of the 97 kD and 70 kD digests were electrophoresed on reducing SDS-PAGE using a 14% acrylamide, Tricine-buffered gel. The gels were blotted using a PVDF membrane (Pro-Blot, Applied Biosystems) and visualized by Coomassie Blue staining. Duplicate lanes were analyzed for $^{125}$I-PHA binding. The remaining two thirds of each of the digests were chromatographed by RP-HPLC using a Vydac C$_4$ column with acetonitrile/iFA as the mobile phase. An aliquot of each column fraction was lyophilized, and analyzed by SDS-PAGE on a 14% acrylamide Tricine-buffered gel, and the remaining protein in each fraction was N-terminally sequenced. Lys-C protease digestion of both the 97 kD and 70 kD molecules produced similar digestion patterns, providing evidence that these molecules are structurally related. Four RP-HPLC peaks were selected, and one, termed peak I, was sequenced using an Applied Biosystems gas phase sequencer following transfer to PVDF membrane. The peptide in peak I generated the N-terminal amino acid sequence set forth in (SEQ ID NO: 2).

From the amino acid sequence of peptide I, three degenerate oligonucleotide primers were synthesized that correspond, in part, to various regions of the peptide. The oligonucleotides were used to prime PCR reactions on SK-BR-3 poly A+mRNA. The degeneracy was decreased somewhat by substituting some selected wobble positions with inosine. The oligonucleotides have the following sequences: (SEQ ID NO: 3); (SEQ ID NO: 4); and (SEQ ID NO. 5).

The underlining marks the positions of restriction sites for HindIII for (SEQ ID NO: 3) and EcoRI for (SEQ ID NO: 4) and (SEQ ID NO: 5). The restriction sites were included in the design of the primers to facilitate cloning the PCR products into pUC vectors.

The PCR reaction was conducted using (SEQ ID NO: 3) in combination with (SEQ ID NO: 4) or (SEQ ID NO: 5).

Briefly, PCR was performed at a final concentration of 1×PCR buffer, 50 μM dNTP's, 1 μM each of 5' and 3' primers, and 1 unit of Taq polymerase in a total volume of 50 μl. Reaction mixtures were heated to 80° C. before adding Taq polymerase. Amplification was performed using two combined cycle formats. The initial 5 cycles of amplification consisted of: denaturation for 30 seconds at 95° C., annealing for 30 seconds at 45° C. and extension for 30 seconds at 72° C. This was followed by 30 cycles of amplification that consisted of denaturation for 30 seconds at 95° C., annealing for 30 seconds at 55° C. and extension for 30 seconds at 72° C.

The predicted PCR products were anticipated to differ by about 24 base pairs, and indeed, the products obtained were approximately 97 and 121 base pairs in length as judged by gel electrophoretic mobility.

The amino-terminal amino acid sequence of the SK-BR-3 gp97 was determined as described above, and these data were used to synthesize additional oligonucleotide primers that were used in subsequent PCR reactions with the primers (SEQ ID NO: 4), and (SEQ ID NO: 5).

The oligonucleotide primer based, in parn, on the amino-terminal sequence is set forth in (SEQ ID NO: 6) and was designed as described above.

The PCR reactions using (SEQ ID NO: 6) and either (SEQ ID NO: 4) or (SEQ ID NO: 5) yielded DNA sequences of about 740 and 765 bases, respectively.

A DNA sequence was obtained from material generated in the above PCR reactions. Two additional oligonucleotide sequences were synthesized, based on this sequence, and used to probe a THP-1 cDNA library to identify a clone that contains the sequence encoding full-length gp97. These oligonucleotide sequences are (SEQ ID NO: 7) and (SEQ ID NO: 8).

EXAMPLE 3

Screening of cDNA Library for gp85–97

A cDNA library was made from mRNA isolated from THP-1 cells induced with 100 ng/ml mezerein for 24 hours. The procedure consisted of isolating the mRNA using procedures described above and conducting first-strand cDNA synthesis by priming with oligo (dT) covalently attached to linearized plasmid, pcDL-SRα296.

Poly (dT) tailing was conducted using 10×terminal deoxynucleotidyl transferase buffer (hereinafter referred to as 10×TdT buffer) which is prepared as follows: 13.8 g cacodylic acid is added to 3.0 g Tris-base in 60 ml of water. The solution is adjusted to pH 7.6 by slQw addition of solid KOH, after which the volume is increased to 88 ml with water. Subsequently, the solution is chilled to 0° C., then 2 ml of 0.1 M DTT is added, followed by the addition of 10 ml of 0.1 M $MnCl_2$ dropwise while the solution is being constantly stirred. To the 20 μl of 10×TdT buffer is added 5.0 μl of 10 mM dTTP, and 200 μg of the Kpn endonuclease-digested pcDL-SRα296 plasmid. An amount of water is added to bring the solution to a total volume of 200 μl. The solution is warmed to 37° C. for 15 minutes, and 360 units of TdT in about 3 μl is added and incubated at 37° C. for 5 minutes.

Next, cDNA synthesis is conducted using reverse transcriptase, as is known in the art, and (dC) tails added to the 3' hydroxyl terminus end of the newly synthesized cDNA. The (dC) tail added during the reaction to the 3' end of pcDL-SRα296 was removed by digestion with HindIII. 100 μl of the reverse transcriptase reaction contained 10 μg of poly (A+) THP-1 RNA, 20 mM Tris-HCl, pH 8.3, 2.5 mM $MgCl_2$, 50 mM KCl, 1 mM DTT, 0.5 mM each 100 units of RNAsin 5 μg of the poly (dT) singly tailed vector-primer DNA and 100 and units of reverse transcriptase. The reaction was run for 30 minutes at 37° C.

Finally, the oligo (dC) tailed cDNA-mRNA plasmid was circularized with a SRα promoter-linker that carried a HindIII site at one end and a homopolymeric tail of dG at the other. The annealing reaction was conducted under standard conditions, using an annealing solution consisting of 10×annealing buffer. The 10×annealing buffer consists of: 0.1 M Tris-HCL, pH 7.6, 1.0 M NaCl, 10 mM EDTA. The mRNA strand was replaced by DNA by sequentially using *E. coli* RNase H, DNA polymerase I and DNA ligase. The DNA was then transformed into DH5-α bacteria. (DH5-α bacteria are obtained from Bethesda Research Laboratories, Research Products Division, Life Technologies, Inc., Gaithersburg, Md. 20877. Cat. No. 82585A: Max Efficiency DH5-α competent cells.)

The cDNA library obtained above may be amplified using procedures well known in the art, and the library may be stored by suspending cell pellets in 12.5% glycerol in LB media at −70° C.

The cDNA library was screened by plating $1.65 \times 10^5$ transformants and using the oligonucleotide with(SEQ ID NO: 8). Thirty-one (31) colonies were positive and were further analyzed by PCR using the primers (SEQ ID NO: 7) and (SEQ ID NO: 8). Of the 31 positive colonies, 7 were found to have approximately the predicted number of base pairs, 437. Two of the 7 clones, clones 17 and 18, were chosen for further study.

Both strands of clone 18 were sequenced, using $\alpha$-$^{35}$S and the Sanger dideoxy method described above. Sequenase was employed as the polymerase. The DNA sequence derived from the clone is set forth in (SEQ ID NO: 9). Nucleotides 180–1934 encode the pro form of gp85–97. Nucleotides 234–1934 encode the mature form of gp85–97. The deduced amino acid sequence is set forth in (SEQ ID NO: 10). Amino acids 1–18 make up the putative leader sequence.

The DNA sequence of the gp85–97 gene encodes a mature protein of sufficient size and complexity that it might be predicted to have multiple functions. Homology searches of the DNA and protein databases reveal the presence of a remarkably conserved domain in the N-terminal region of human gp85–97. The first 105 amino acids of the mature gp85–97 protein are over 50% identical to the extracellular terminal sequence of the type I human macrophage scavenger receptor. Kodama, T., et al., 1990, *Nature*, 34:531–535. The exact function of this domain is presently unknown, but other domains of the scavenger receptor are apparently involved in removal of undesirable molecules such as oxidized low density lipoprotein, bacterial lipopolysaccharide, and single-stranded nucleic acid. This same domain is highly conserved between gp85–97 and sea urchins where it is found duplicated on the surface of sperm and appears to function as a receptor for a sperm-activating egg peptide. Dangott, L., e al., 1989, *PNAS (USA)*, 86:2128. The gp85–97 N-terminal domain is also significantly homologous to other human proteins such as the lymphocyte glycoprotein CD6. Thus, gp85–97 may exhibit functions similar to these homologous proteins, such as involvement in responding to infectious diseases or promoting immune responses. The mature N-terminal sequence and apparent molecular mass of gp85–97 are identical to that of an as yet uncloned lung carcinoma glycoprotein, the L3 antigen. Linsley et al., *Biochemistry* (1986) 25:2978–2986.

EXAMPLE 4

Expression of SK-BR-3 gp97

Two full-length clones, clone 17 and 18, were transfected into the cell line, Cos A2. Cell line "Cos A2" a soft-agar subclone of Cos-1 cells (Gluzman, Y., 1981, *Cell*, 23:175–182). Cells in log phase were transfected using 0.05% DEAE Dextran (Sompayrac, L. M. et al., 1981, *PNAS (USA)*, 78:7575–7578) with the appropriate plasmid. The cells were incubated at room temperature for 1 hour and then washed to remove residue DEAE-plasmid, and growth media was added that contained 100 μM chloroquine. After 4 hours of incubation at 37° C. in an atmosphere of 5% $CO_2$/95% air, the media was removed and replaced with fresh growth media without chloroquine. The cells were incubated in a tissue culture incubator, and media was harvested at 24, 48, and 72 hours.

Figure 5:
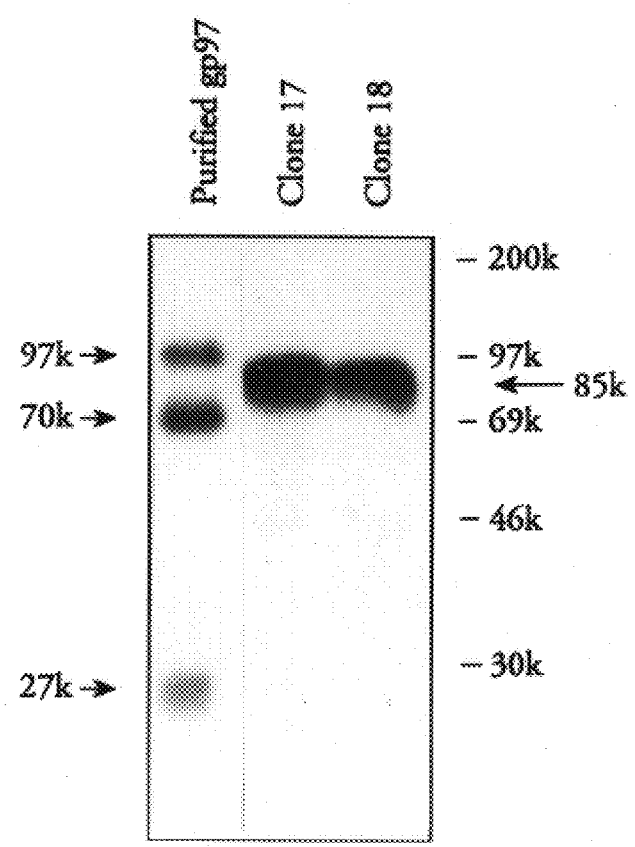
FIG. 5 shows Western blot analysis of COS cell-expressed gp85–97.

The media from the 72-hour incubations was cleared by centrifugation immediately after harvesting and frozen for further analysis. The gp97 protein in 1 ml of the culture supernatant was immunoprecipitated by binding to purified anti-gp85–97 antibody coupled to 40 μl of Affigel 10 beads (BioRad). The bound protein was released from the pelleted, washed beads by boiling in 20 μl of non-reducing SDS-PAGE sanipled buffer. After removal of the beads, samples were reduced by boiling in the presence of added 2-mercaptoethanol (1%) and assayed by Western blotting using affinity purified $^{125}$I-labelled anti-gp85–97 antibody as described above. The antibody was produced as described below. The results are shown in FIG. 5. It is apparent from the figure that gp97 antibody-reactive material is produced by both clones. It is possible that the observed 85 kD molecular weight differs from that of the SK-BR-3 gp97 standard because of differences in glycosylation.

EXAMPLE 5

Antibody to SK-BR-3 gp97

An immunization procedure using native SK-BR-3 gp97 (purified as described above through the sucrose gradient step) was carried out over several months. Immunization was initiated with about 200 μg of material. About 20 days after this immunization, rabbits were boosted with about 100 μg of the material, and bled 10 days later. This boosting/bleeding procedure was conducted for several months. The initial immunization of about 200 μg was carried out in complete Freund's adjuvant by injection into the popliteal nodes of New Zealand white rabbits, while the subsequent boosts were given intramuscularly in Incomplete Freund's adjuvant. At the end of the seventh month, the rabbits were exsanguinated and the serum isolated. Antibody was purified by affinity chromatography on a protein A Sepharose column. (Pharmacia LKB Biotechnology, Inc.) For some experiments the anti-gp85–97 antibody was further purified by ligand affinity chromatography utilizing 97 kD and 70 kD glycopeptides purified by high-performance electrophoretic chromatography and coupled to Affigel 10/15 (BioRad). Purified antibody was eluted with glycine/HCl, pH 2.

Studies were conducted to determine if antibody generated against SK-BR-3 gp97 would have neutralizing activity. The antibody was tested for its neutralizing titer against gp97 in two cell-based assays, as well as the $^{125}$I-PHA dot-blot assay described above. At a dilution of 1/40, the antibody was capable of a 50% neutralization of a 20 μg/ml solution of gp97, as measured by cell-based biological assays. Since antibody in the absence of gp97 had no effect in the assay, it is apparent that antibody is neutralizing the effects of the gp97. The relatively low neutralizing titer of the antibody may reflect multiple binding sites on what is believed to be a large, multi-subunit protein complex. Similar dilutions of the antibody neutralized $^{125}$I-PHA binding to a similar amount of immobilized native gp97.

The antibody to SK-BR-3 gp97 was tested for its ability to react with gp85–97 in various biological samples. Using Western or dot-blot analysis the antibody reacted with semi-purified material from human serum and purified material from human milk. Material from fresh human serum eluted at or near the void volume on SEC-HPLC and was thus similar to material purified from SK-BR-3 cells.

EXAMPLE 6

Purification of gp85 From Human Breast Milk 400 milliliters of human milk was pooled from multiple anonymous donors and shown to be negative for HIV and hepatitis B virus. The milk was adjusted to contain 1 mM EDTA, 1 μg/ml leupeptin, and 200 μM PMSF. These inhibitors at these concentrations were used throughout the purification.

The milk was defatted by two centrifugations at 25,000×g for 30 minutes at 4° C. and removal of the upper fat layer followed by filtration of the aqueous layer through a glass fiber filter, and subsequent filtration through a Gelman 50A 5 μm filter. The filtrate was made 0.5 M in ammonium sulfate (pH 7.0) and chromatographed over a 5×20 cm Phenyl-Sepharose (Pharmacia) column. The protein was eluted from the column at 10 ml/min with a criss-crossing gradient of decreasing ammonium sulfate and increasing ethylene glycol from 0–30%. The column flow-through was re-chromatographed over the same column. Fractions enriched for gp85 were pooled from both columns, dialyzed into PBS, and concentrated 30-fold with an Amicon stir cell using a YM30 membrane.

The Amicon-concentrate material was divided into two 25 ml aliquots and each was separately chromatographed over a S300 Sephacryl (Pharmacia) size exclusion column having the dimensions of 5×90 cm. Protein was eluted from the column at 5 ml/min. Peak fractions of gp85 were pooled, and concentrated 30-fold as above.

Next, 2 ml aliquots of the concentrated material were layered on a 37 ml, 5–50% sucrose gradient buffered with PBS and centrifuged in a Beckman SW28 rotor at 27,000 rpm at 15° C. for 23 hours. The bottom of the tube was punctured and fractions collected therefrom.

Figure 6A:
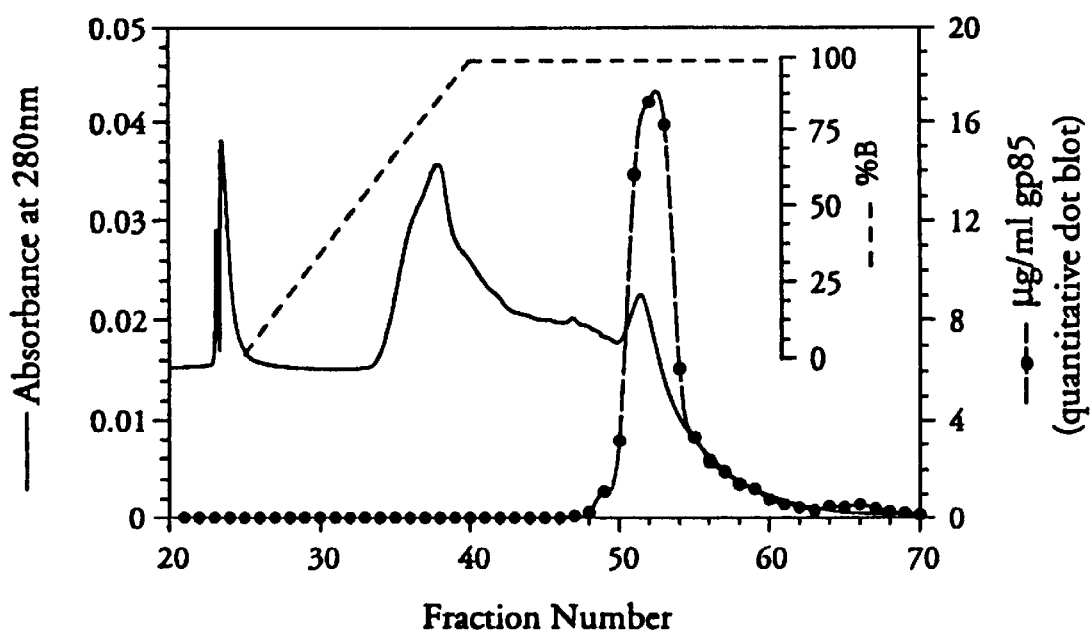
FIG. 6A shows a phenyl TSK HPLC chromatographic profile of gp 85 from human breast milk.
Figure 6B:
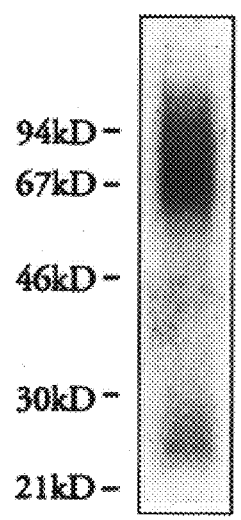
FIG. 6B shows a SDS-PAGE analysis of the peak fraction.

Two-fifths of the peak fractions of gp85 was dialyzed into 50 mM Tris pH 8, 150 mM NaCl containing 0.1 mM EDTA instead of 1 mM. The retentate was made 1 mM in $MgCl_2$, $CaCl_2$, and $MnCl_2$ followed by the addition of 20 ml bed volume of pre-washed Lentil Lectin Sepharose (Pharmacia). The mixture was incubated with shaking at 4° C. for 3 hours, poured into a 2.6 cm diameter column and washed at ambient temperature with 50 mM Tris pH 8, 150 mM NaCl minus EDTA. The column was eluted with 200 mM α-methyl-D-mannopyranoside in the same buffer. The eluted gp85 was made 0.8 M in ammonium sulfate, pH 7.0 and chromatographed over an analytical Phenyl-TSK HPLC column (BioRad) having the dimensions of 7.5×75 mm. Protein was eluted from the column at a flow rate of 1 ml/min under the conditions described above. For SDS-PAGE analysis, entire fractions were dialyzed into 0.1% SDS buffered with 1 mM Tris pH 7.5, lyophilized, and resuspended in 15 μl reducing sample buffer. Bands were visualized by staining with Coomassie Brilliant Blue. The column profile and SDS-PAGE analysis are shown in FIGS. 6A and 6B, respectively. The heterogeneous distribution of apparent subunit molecular weights from about 60 kD to over 100 kD probably reflects heterogeneity in glycosylation.

A second aliquot of the purified preparation was fractionated on SDS-PAGE as described above and transferred to PVDF membrane as described in the SK-BR-3 70 kD fragment isolation of Example 1. The N-terminal sequence obtained using an Applied Biosystems 470A Gas-Phase Sequencer was as follows: (SEQ ID NO: 11).

The remaining three-fifths of the sucrose gradient peak fractions was subjected to lentil-lectin chromatography as described above except that the column was eluted at 4° C. followed by an identical elution at ambient temperature, which released additional bound protein. The gp85 that eluted at 4° C. was chromatographed using analytical Phenyl-TSK HPLC as above. Fractions enriched for gp85 were pooled, dialyzed into PBS, concentrated 10-fold and stored at −20° C. The gp85 that eluted at ambient temperature was concentrated 75-fold using an Amicon YM30 membrane, and the retentate was chromatographed over a Pharmacia Superose 6 size-exclusion FPLC column. The protein was eluted from the column at 0.5 ml/min with a mobile phase of PBS. Peak fractions of gp85 were pooled, concentrated 2-fold, filter-sterilized, and stored at 4° C. Starting with defatted, filtered human milk, the purification protocol yielded 400 μg of gp85 purified 1300-fold with about 6% recovery.

In addition to the characterization of gp85 described above, the material purified by Superose 6 chromatography was analyzed by sucrose gradient sedimentation velocity as described in Example 1. The sedimentation value of material that reacted with anti-gp85–97 antibody in a dot-blot assay was approximately 25. Additional reactive material was detected with a sedimentation value of over 30.

EXAMPLE 7

Growth Inhibition of Breast Cancer Cells

Neutralizing antibody obtained as described in Example 5 was tested for cancer cell growth-inhibitory activity. The assay consisted of determining the effect dilutions of a protein-A-purified anti-gp85–97 antibody on cell growth as a function of thymidine incorporation. The human breast tumor cell line, SK-BR-3 was tested under conditions of minimal stimulation in nutrient-deficient medium (RPMI with limiting fetal calf serum). An anti-GAP polyclonal antibody (Halenbeck, R. et al., 1990, *J. Biol. Chem.*, 265:21922–21928) was used as a control following an identical protein A purification.

The thymidine assay was conducted as follows: SK-BR-3 cell proliferation was measured by adding 2 μCi/per well of $^3$H-thymidine and incubating the cells for 4 hours at 37° C., after which the cells were washed, harvested, and counted using standards. The assay was conducted twice, with all samples being assayed in quintuplicate. The results are shown in Table 1.

TABLE 1

| Treatment | % of Control |
|---|---|
| Experiment 1* (Control = 3156 CPM) | |
| Control (Media) | 100 +/− 12 |
| Purified SK-BR-3 gp97 1:10 (0.05 mg/ml) | 104 +/− 3 |
| Purified SK-BR-3 gp97 1:40 | 105 +/− 5 |
| Purified Anti-gp85-97 Antibody 1:10 (0.1 mg/ml) | 32 +/− 3 |
| Antibody 1:40 | 40 +/− 3 |
| Purified Control Antibody 1:10 (0.1 mg/ml) | 97 +/− 8 |
| Purified Control Antibody 1:40 | 155 +/− 5 |
| Experiment 2* (Control = 2009 CPM) | |
| Control | 100 +/− 8 |
| gp85-97 Antibody 1:10 | 43 +/− 4 |
| gp85-97 Antibody 1:40 | 51 +/− 11 |

*All samples assayed in quintuplicate

In the first experiment, relative to the controls, which consisted of media without antibody or the antigen used to generate the antibody, gp97, there was a 68% and 60% reduction in the amount of $^3$H-thymidine uptake at antibody dilutions of 1:10 and 1:40, respectively. A control antibody was shown to have essentially no effect or a stimulatory effect on $^3$H-thymidine uptake.

In the second experiment, there was a 57% and 49% reduction in the amount of $^3$H-thymidine uptake at antibody dilutions of 1:10 and 1:40, respectively.

EXAMPLE 8

Detection of gp85–97 in Human Fluids

Assorted human fluids were immunoprecipitated with anti-gp85–97 antibody (as prepared above) and subjected to Western analysis (FIG. 7). Lanes 1–7, respectively, are: buffer control; semen, 0.5 ml; breast milk, 0.05 ml; plasma, 1.0 ml; saliva, 0.5 ml; tears, 0.2 ml; and urine, 1.0 ml. Samples were adjusted to 0.1 mM PMSF and 2 μg/ml leupeptin in a final volume of 1 ml of PBS. These solutions were immunoprecipitated and subjected to non-reducing SDS-PAGE and Western analysis using affinity-purified $^{125}$I-labelled anti-gp85–97 antibody as described in Example 1-B. Immunoreactive material varied somewhat in size and complexity, but generally contained two bands between 60 and 100 kDa $M_r$. The fact that the immunoreactive material in breast milk was purified using the same antibody for assay detection and had the N-terminal sequence of gp85–97 (see above) argues that immunoreactive bands of similar size in other human fluids also represent gp85–97.

EXAMPLE 9

Co-Precipitation of gp85–97

HT-29 cells (ATCC HTB 38) were grown, lysed with 0.5% Triton X-100, centrifuged to remove cells and debris, immunoprecipitated using anti-Mac-2 monoclonal antibody (M3/38, Boehringer Mannheim) and protein G Sepharose (Pharmacia), essentially as previously described (Rosenberg et al., *J. Biol. Chem.* (1991) 2:18731–18736). Immunoprecipitations were also performed using purified polyclonal rabbit antibody to gp85–97, immobilized on Affigel 10. HL-60 cells (ATCC CCL 240) were differentiated with 80 mM phorbol 12-myristate 13-acetate for 72 hours and lysed as above.

Immunoprecipitates were analyzed by non-reducing or reducing (lanes probed with Mac-2 antibody) SDS-PAGE and Western analysis with $^{125}$I-labelled antibodies (Probe Ab) as shown in FIG. 8. Samples marked (+lac) and (+man) received 0.25 M lactose or mannose, respectively, prior to precipitation. The first lane in each panel shows background from immunoprecipitation of lysis buffer. FIG. 8A) Lysate of human colon carcinoma, HT-29 (1.5 mg/lane). FIG. 8B) Purified gp97 (5 μg) mixed with lysate of human promyelocytic leukemia, HL-60 (0.8 mg/lane). FIG. 8 shows that gp85–97 is bound by the human Mac-2 lectin via its lactose-dissociable, carbohydrate binding properties.

| Deposition of Cultures | | |
|---|---|---|
| Vector | Deposit Date | ATCC Accession No. |
| pSKBR3-gp97 | April 30, 1991 | 68608 |

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 12 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:1:

```
Val Asn Asp Gly Asp Met Arg Leu Ala Asp Gly Gly
1               5                   10
```

(2) INFORMATION FOR SEQ ID NO:2:

(i) SEQUENCE CHARACTERISTICS:
      (A) LENGTH: 38 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:2:

```
Leu Ala Ser Ala Tyr Gly Ala Arg Gln Leu Gln Gly Tyr Leu Ala Ser
1               5                   10                  15

Leu Phe Ala Ile Leu Leu Pro Gln Asp Pro Ser Phe Gln Met Ser Leu
            20                  25                  30

Asp Leu Tyr Ala Tyr Ala
            35
```

(2) INFORMATION FOR SEQ ID NO:3:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: cDNA to mRNA (ix) FEATURE:
      (A) NAME/KEY: misc_difference
      (B) LOCATION: replace(11..12, "")
      (D) OTHER INFORMATION: /note= "N = INOSINE"

(ix) FEATURE:
      (A) NAME/KEY: misc_difference
      (B) LOCATION: replace(17..18, "")
      (D) OTHER INFORMATION: /note= "N = INOSINE"

(ix) FEATURE:
      (A) NAME/KEY: misc_difference
      (B) LOCATION: replace(20..21, "")
      (D) OTHER INFORMATION: /note= "N = INOSINE"

(ix) FEATURE:
      (A) NAME/KEY: misc_difference
      (B) LOCATION: replace(23..24, "")
      (D) OTHER INFORMATION: /note= "N = INOSINE"

(xi) SEQUENCE DESCRIPTION: SEQ ID NO:3:

CAAGCTTGGC NTAYGGNGCN MGNCA                              25

(2) INFORMATION FOR SEQ ID NO:4:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA to mRNA (ix) FEATURE:
        (A) NAME/KEY: misc_difference
        (B) LOCATION: replace(18..19, "")
        (D) OTHER INFORMATION: /note= "N = INOSINE"

(ix) FEATURE:
        (A) NAME/KEY: misc_difference
        (B) LOCATION: replace(21..22, "")
        (D) OTHER INFORMATION: /note= "N = INOSINE"

(xi) SEQUENCE DESCRIPTION: SEQ ID NO:4:

GGAATTCCCA TYTGRAANSW NGGRTC                          26

(2) INFORMATION FOR SEQ ID NO:5:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA to mRNA (ix) FEATURE:
        (A) NAME/KEY: misc_difference
        (B) LOCATION: replace(14..15, "")
        (D) OTHER INFORMATION: /note= "N = INOSINE"

(ix) FEATURE:
        (A) NAME/KEY: misc_difference
        (B) LOCATION: replace(20..21, "")
        (D) OTHER INFORMATION: /note= "N = INOSINE"

(xi) SEQUENCE DESCRIPTION: SEQ ID NO:5:

GGAATTCCGC RTANGCRTAN ARRTC                           25

(2) INFORMATION FOR SEQ ID NO:6:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA to mRNA (ix) FEATURE:
        (A) NAME/KEY: misc_difference
        (B) LOCATION: replace(13..14, "")
        (D) OTHER INFORMATION: /note= "N = INOSINE"

(ix) FEATURE:
        (A) NAME/KEY: misc_difference
        (B) LOCATION: replace(22..23, "")
        (D) OTHER INFORMATION: /note= "N = INOSINE"

(xi) SEQUENCE DESCRIPTION: SEQ ID NO:6:

GGGCAAGCTT GTNAAYGAYG GNGAYATG                       28

(2) INFORMATION FOR SEQ ID NO:7:

(i) SEQUENCE CHARACTERISTICS:
        (A) LENGTH: 19 base pairs (B) TYPE: nucleic acid
        (C) STRANDEDNESS: single
        (D) TOPOLOGY: linear (ii) MOLECULE TYPE: cDNA to mRNA (xi) SEQUENCE DESCRIPTION: SEQ ID NO:7:

GAGAACGCCA CCCAGGCTC                                                  19

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA to mRNA (xi) SEQUENCE DESCRIPTION: SEQ ID NO:8:

AGAAGTACCT GAGAAGGTCC                                                 20

(2) INFORMATION FOR SEQ ID NO:9:

(i) SEQUENCE CHARACTERISTICS:
        (A) LENGTH: 2285 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

AATCGAAAGT AGACTCTTTT CTGAAGCATT TCCTGGGATC AGCCTGACCA CGCTCCATAC      60

TGGGAGAGGC TTCTGGGTCA AGGACCAGT CTGCAGAGGG ATCCTGTGGC TGGAAGCGAG      120

GAGGCTCCAC ACGGCCGTTG CAGCTACCGC AGCCAGGATC TGGGCATCCA GGCACGGCCA     180

TGACCCCTCC GAGGCTCTTC TGGGTGTGGC TGCTGGTTGC AGGAACCCAA GGCGTGAATG     240

ATGGTGACAT GCGGCTGGCC GATGGGGGCG CCACCAACCA GGGCCGCGTG GAGATCTTCT     300

ACAGAGGCCA GTGGGGCACT GTGTGTGACA ACCTGTGGGA CCTGACTGAT GCCAGCGTCG     360

TCTGCCGGGC CCTGGGCTTC GAGAACGCCA CCCAGGCTCT GGGCAGAGCT GCCTTCGGGC     420

AAGGATCAGG CCCCATCATG CTGGACGAGG TCCAGTGCAC GGGAACCGAG GCCTCACTGG     480

CCGACTGCAA GTCCCTGGGC TGGCTGAAGA GCAACTGCAG GCACGAGAGA GACGCTGGTG     540

TGGTCTGCAC CAATGAAACC AGGAGCACCC ACACCCTGGA CCTCTCCAGG GAGCTCTCGG     600

AGGCCCTTGG CCAGATCTTT GACAGCCAGC GGGGCTGCGA CCTGTCCATC AGCGTGAATG     660

TGCAGGGCGA GGACGCCCTG GGCTTCTGTG CCCACACGGT CATCCTGACT GCCAACCTGG     720

AGGCCCAGGC CCTGTGGAAG GAGCCGGGCA GCAATGTCAC CATGAGTGTG GATGCTGAGT     780

GTGTGCCCAT GGTCAGGGAC CTTCTCAGGT ACTTCTACTC CCGAAGGATT GACATCACCC     840

TGTCGTCAGT CAAGTGCTTC CACAAGCTGG CCTCTGCCTA TGGGGCCAGG CAGCTGCAGG     900

GCTACTGCGC AAGCCTCTTT GCCATCCTCC TCCCCCAGGA CCCCTCGTTC CAGATGCCCC     960

TGGACCTGTA TGCCTATGCA GTGGCCACAG GGACGCCCT GCTGGAGAAG CTCTGCCTAC     1020

AGTTCCTGGC CTGAACTTC GAGGCCTTGA CGCAGGCCGA GGCCTGGCCC AGTGTCCCCA     1080

CAGACCTGCT CCAACTGCTG CTGCCCAGGA GCGACCTGGC GGTGCCCAGC GAGCTGGCCC     1140

TACTGAAGGC CGTGGACACC TGGAGCTGGG GGAGCGTGC CTCCCATGAG GAGGTGGAGG     1200

GCTTGGTGGA GAAGATCCGC TTCCCCATGA TGCTCCCTGA GGAGCTCTTT GAGCTGCAGT     1260

```
TCAACCTGTC CCTGTACTGG AGCCACGAGG CCCTGTTCCA GAAGAAGACT CTGCAGGCCC    1320

TGGAATTCCA CACTGTGCCC TTCCAGTTGC TGGCCCGGTA CAAAGGCCTG AACCTCACCG    1380

AGGATACCTA CAAGCCCCGG ATTTACACCT CGCCCACCTG GAGTGCCTTT GTGACAGACA    1440

GTTCCTGGAG TGCACGGAAG TCACAACTGG TCTATCAGTC CAGACGGGGG CCTTTGGTCA    1500

AATATTCTTC TGATTACTTC CAAGCCCCCT CTGACTACAG ATACTACCCC TACCAGTCCT    1560

TCCAGACTCC ACAACACCCC AGCTTCCTCT TCCAGGACAA GAGGGTGTCC TGGTCCCTGG    1620

TCTACCTCCC CACCATCCAG AGCTGCTGGA ACTACGGCTT CTCCTGCTCC TCGGACGAGC    1680

TCCCTGTCCT GGGCCTCACC AAGTCTGGCG GCTCAGATCG CACCATTGCC TACGAAAACA    1740

AAGCCCTGAT GCTCTGCGAA GGGCTCTTCG TGGCAGACGT CACCGATTTC GAGGGCTGGA    1800

AGGCTGCGAT TCCCAGTGCC CTGGACACCA ACAGCTCGAA GAGCACCTCC TCCTTCCCCT    1860

GCCCGGCAGG GCACTTCAAC GGCTTCCGCA CGGTCATCCG CCCCTTCTAC CTGACCAACT    1920

CCTCAGGTGT GGACTAGACG GCGTGGCCCA AGGGTGGTGA GAACCGGAGA ACCCCAGGAC    1980

GCCCTCACTG CAGGCTCCCC TCCTCGGCTT CCTTCCTCTC TGCAATGACC TTCAACAACC    2040

GGCCACCAGA TGTCGCCCTA CTCACCTGAG CGCTCAGCTT CAAGAAATTA CTGGAAGGCT    2100

TCCACTAGGG TCCACCAGGA GTTCTCCCAC CACCTCACCA GTTTCCAGGT GGTAAGCACC    2160

AGGACGCCCT CGAGGTTGCT CTGGGATCCC CCCACAGCCC CTGGTCAGTC TGCCCTTGTC    2220

ACTGGTCTGA GGTCATTAAA ATTACATTGA GGTTCCTAAA AAAAAAAAAA AAAAAAAAA    2280

AAAAA                                                                2285

(2) INFORMATION FOR SEQ ID NO:10:

(i) SEQUENCE CHARACTERISTICS:
        (A) LENGTH: 585 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:10:

Met Thr Pro Pro Arg Leu Phe Trp Val Trp Leu Leu Val Ala Gly Thr
1               5                   10                  15

Gln Gly Val Asn Asp Gly Asp Met Arg Leu Ala Asp Gly Gly Ala Thr
            20                  25                  30

Asn Gln Gly Arg Val Glu Ile Phe Tyr Arg Gly Gln Trp Gly Thr Val
        35                  40                  45

Cys Asp Asn Leu Trp Asp Leu Thr Asp Ala Ser Val Val Cys Arg Ala
    50                  55                  60

Leu Gly Phe Glu Asn Ala Thr Gln Ala Leu Gly Arg Ala Ala Phe Gly
65                  70                  75                  80

Gln Gly Ser Gly Pro Ile Met Leu Asp Glu Val Gln Cys Thr Gly Thr
                85                  90                  95

Glu Ala Ser Leu Ala Asp Cys Lys Ser Leu Gly Trp Leu Lys Ser Asn
            100                 105                 110

Cys Arg His Glu Arg Asp Ala Gly Val Val Cys Thr Asn Glu Thr Arg
        115                 120                 125

Ser Thr His Thr Leu Asp Leu Ser Arg Glu Leu Ser Glu Ala Leu Gly
    130                 135                 140

Gln Ile Phe Asp Ser Gln Arg Gly Cys Asp Leu Ser Ile Ser Val Asn
145                 150                 155                 160

Val Gln Gly Glu Asp Ala Leu Gly Phe Cys Gly His Thr Val Ile Leu
```

```
                    165                 170                 175
Thr Ala Asn Leu Glu Ala Gln Ala Leu Trp Lys Glu Pro Gly Ser Asn
                180                 185                 190
Val Thr Met Ser Val Asp Ala Glu Cys Val Pro Met Val Arg Asp Leu
            195                 200                 205
Leu Arg Tyr Phe Tyr Ser Arg Arg Ile Asp Ile Thr Leu Ser Ser Val
        210                 215                 220
Lys Cys Phe His Lys Leu Ala Ser Ala Tyr Gly Ala Arg Gln Leu Gln
225                 230                 235                 240
Gly Tyr Cys Ala Ser Leu Phe Ala Ile Leu Leu Pro Gln Asp Pro Ser
                245                 250                 255
Phe Gln Met Pro Leu Asp Leu Tyr Ala Tyr Ala Val Ala Thr Gly Asp
            260                 265                 270
Ala Leu Leu Glu Lys Leu Cys Leu Gln Phe Leu Ala Trp Asn Phe Glu
        275                 280                 285
Ala Leu Thr Gln Ala Glu Ala Trp Pro Ser Val Pro Thr Asp Leu Leu
290                 295                 300
Gln Leu Leu Leu Pro Arg Ser Asp Leu Ala Val Pro Ser Glu Leu Ala
305                 310                 315                 320
Leu Leu Lys Ala Val Asp Thr Trp Ser Trp Gly Glu Arg Ala Ser His
                325                 330                 335
Glu Glu Val Glu Gly Leu Val Glu Lys Ile Arg Phe Pro Met Met Leu
            340                 345                 350
Pro Glu Glu Leu Phe Glu Leu Gln Phe Asn Leu Ser Leu Tyr Trp Ser
        355                 360                 365
His Glu Ala Leu Phe Gln Lys Lys Thr Leu Gln Ala Leu Glu Phe His
    370                 375                 380
Thr Val Pro Phe Gln Leu Leu Ala Arg Tyr Lys Gly Leu Asn Leu Thr
385                 390                 395                 400
Glu Asp Thr Tyr Lys Pro Arg Ile Tyr Thr Ser Pro Thr Trp Ser Ala
                405                 410                 415
Phe Val Thr Asp Ser Ser Trp Ser Ala Arg Lys Ser Gln Leu Val Tyr
            420                 425                 430
Gln Ser Arg Arg Gly Pro Leu Val Lys Tyr Ser Ser Asp Tyr Phe Gln
        435                 440                 445
Ala Pro Ser Asp Tyr Arg Tyr Tyr Pro Tyr Gln Ser Phe Gln Thr Pro
450                 455                 460
Gln His Pro Ser Phe Leu Phe Gln Asp Lys Arg Val Ser Trp Ser Leu
465                 470                 475                 480
Val Tyr Leu Pro Thr Ile Gln Ser Cys Trp Asn Tyr Gly Phe Ser Cys
                485                 490                 495
Ser Ser Asp Glu Leu Pro Val Leu Gly Leu Thr Lys Ser Gly Gly Ser
            500                 505                 510
Asp Arg Thr Ile Ala Tyr Glu Asn Lys Ala Leu Met Leu Cys Glu Gly
        515                 520                 525
Leu Phe Val Ala Asp Val Thr Asp Phe Glu Gly Trp Lys Ala Ala Ile
    530                 535                 540
Pro Ser Ala Leu Asp Thr Asn Ser Ser Lys Ser Thr Ser Ser Phe Pro
545                 550                 555                 560
Cys Pro Ala Gly His Phe Asn Gly Phe Arg Thr Val Ile Arg Pro Phe
                565                 570                 575
Tyr Leu Thr Asn Ser Ser Gly Val Asp
            580                 585
```

(2) INFORMATION FOR SEQ ID NO:11:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:11:

```
Val Asn Asp Gly Asp Met Arg Leu Ala Asp Gly Gly Ala Thr Asn Gln
1               5                  10                 15

Gly Arg Val Glu Ile Phe Tyr
            20
```

The present invention has been described with reference to specific embodiments. However, this application is intended to cover those changes and substitutions which may be made by those skilled in the art without departing from the spirit and the scope of the appended claims.

We claim:

1. An isolated DNA that encodes a protein comprising the amino acid sequence of residues 230–267 of SEQ ID NO:10.

2. A DNA as described in claim 1, said DNA comprising SEQ ID NO:9.

3. A method of producing a protein, said method comprising the steps of:
    a) transforming a host cell with a nector comprising the DNA of claim 1,
    b) cultivating said host cell under conditions that allow expression of said DNA and production of said protein encoded by said DNA; and
    c) recovering said protein.

4. An isolated nucleic acid comprising at least 20 contiguous nucleotides of nucleotides 180–1934 of SEQ ID NO:9 or of the complement thereof.

5. The nucleic acid of claim 4, wherein said nucleic acid has the nucleotide sequence of SEQ ID NO:8.

6. The nucleic acid of claim 4, wherein said nucleic acid is 740 nucleotides in length.

7. The nucleic acid of claim 4, wherein said nucleic acid is 765 nucleotides in length.

8. The nucleic acid of claim 4, wherein said nucleic acid is 437 nucleotides in length.

9. The nucleic acid of claim 4, wherein said nucleic acid is 121 nucleotides in length.

10. The nucleic acid of claim 4, wherein said nucleic acid is 97 nucleotides in length.

11. The nucleic acid of claim 4, wherein said nucleic acid is 20 nucleotides in length.

12. A host cell comprising an exogenous nucleic acid encoding a protein comprising amino acids 230–267 of SEQ ID NO:10.

13. The plasmid pSKBR3-gp97 on deposit with the American Type Culture Collection with accession number 68608.

14. An isolated DNA encoding a protein having an amino acid sequence selected from the group consisting of: SEQ ID NO:10, residues 19–585 of SEQ ID NO:10, and residues 19–124 of SEQ ID NO:10.

15. The DNA of claim 14, wherein said protein has the amino acid sequence of residues 19–585 of SEQ ID NO:10.

16. The DNA of claim 14, wherein said protein has the amino acid sequence of residues 19–124 of SEQ ID NO:10.

17. A method of producing a protein, said method comprising the steps of:
    a) transforming a host cell with a victor comprising the DNA of claim 14
    b) cultivating said host cell under conditions that allow expression of said DNA and production of said protein encoded by said DNA; and
    c) recovering said protein.

18. A vector comprising the DNA of claim 14.

19. An isolated nucleic acid selected from the group consisting of:
    a) a DNA comprising nucleotides 1–2285 of SEQ ID NO:9;
    b) a DNA comprising nucleotides 180–1934 of SEQ ID NO:9;
    c) a DNA comprising nucleotides 234–1934 of SEQ ID NO:9;
    d) a DNA having a nucleotide sequence complementary to a), b), or c); and
    e) an RNA comprising a nucleotide sequence corresponding to said DNA of a), b), c), or d), wherein uracil replaces thymine.

20. The nucleic acid of claim 19, wherein said nucleic acid is a DNA comprising nucleotides 180–1934 of SEQ ID NO:9, or an RNA comprising a nucleotide sequence corresponding to nucleotides 180–1934 of SEQ ID NO:9 wherein uracil replaces thymine.

21. The nucleic acid of claim 19, wherein said nucleic acid is a DNA comprising nucleotides 234–1934 of SEQ ID NO:9, or an RNA comprising a nucleotide sequence corresponding to nucleotides 234–1934 of SEQ ID NO:9 wherein uracil replaces thymine.

22. A vector comprising the nucleic acid of claim 19.

* * * * *